US008653326B2

(12) United States Patent
D'Halluin et al.

(10) Patent No.: US 8,653,326 B2
(45) Date of Patent: *Feb. 18, 2014

(54) TARGETED DNA INSERTION IN PLANTS

(75) Inventors: Kathleen D'Halluin, Mariakerke (BE); Chantal Vanderstraeten, Ghent (BE); Rene Ruiter, Huesden (BE)

(73) Assignee: Bayer Cropscience N.V., Diegem (BE)

( * ) Notice: Subject to any disclaimer, the term of this patent is extended or adjusted under 35 U.S.C. 154(b) by 824 days.

This patent is subject to a terminal disclaimer.

(21) Appl. No.: 12/497,937

(22) Filed: Jul. 6, 2009

(65) Prior Publication Data

US 2010/0003759 A1 Jan. 7, 2010

Related U.S. Application Data

(62) Division of application No. 10/580,078, filed as application No. PCT/EP2004/013122 on Nov. 17, 2004, now Pat. No. 7,598,365.

(30) Foreign Application Priority Data

Nov. 18, 2003 (EP) .................................... 03078700

(51) Int. Cl.
  *C12N 15/82* (2006.01)
(52) U.S. Cl.
  USPC .......................................... 800/278; 435/468
(58) Field of Classification Search
  None
  See application file for complete search history.

(56) References Cited

U.S. PATENT DOCUMENTS

| 5,474,896 | A | * | 12/1995 | Dujon et al. | ................. | 435/6.16 |
| 5,689,052 | A | | 11/1997 | Brown et al. | | |
| 6,140,553 | A | * | 10/2000 | D'Halluin | ..................... | 800/278 |
| 7,598,365 | B2 | * | 10/2009 | D'Halluin et al. | ........... | 536/23.2 |
| 2002/0107214 | A1 | | 8/2002 | Choulika et al. | | |
| 2005/0066384 | A1 | * | 3/2005 | Klimyuk et al. | .............. | 800/278 |

FOREIGN PATENT DOCUMENTS

| CA | 2451492 | 1/2003 |
| EP | 0 242 236 A1 | 10/1987 |
| EP | 0 242 246 A1 | 10/1987 |
| EP | 0 317 509 A2 | 5/1989 |
| WO | 94/01560 A1 | 1/1994 |
| WO | 94/17176 A1 | 8/1994 |
| WO | 94/18313 A1 | 8/1994 |
| WO | 94/26913 | 11/1994 |
| WO | 95/09233 A1 | 4/1995 |
| WO | 96/14408 A2 | 5/1996 |
| WO | WO 98/37212 | 8/1998 |
| WO | 00/46386 A2 | 8/2000 |
| WO | WO 01/13707 | 3/2001 |
| WO | 03/004659 A2 | 1/2003 |
| WO | 03/054189 A2 | 7/2003 |
| WO | 03/080809 A2 | 10/2003 |

OTHER PUBLICATIONS

Koziel et al. Optimizing expression of transgenes with an emphasis on post-transcriptional events. (1996) Plant Molecular Biology; vol. 32; pp. 393-405.*
Puchta et al. Homologous recombination in plant cells is enhanced by in vivo induction of double strand breaks into DNA by a site-specific endonuclease. (1993) Nucleic Acids Research; vol. 21; pp. 5034-5040.*
Forsbach et al. A comprehensive characterization of single-copy T-DNA insertions in the *Arabidopsis thaliana* genome. (2003) Plant Molecular Biology; vol. 52; pp. 161-176.*
D'Halluin, K. et al., "Homologous Recombinattion: A Basis for Targeted Genome Optimization in Crop Species Such as Maize", Plant Biotechnology Journal, vol. 6, pp. 93-102, Jan. 2008.
Reiss, B. et al., "Targeting of a Functional *Escherichia coli* RecA Protein to the Nucleus of Plant Cells" Molecular Genetics and Genomics, vol. 253, pp. 695-702, Jan. 1997.
Ashby, et al. "Ti Plasmid-Specified Chemotaxis of *Agrobacterium tumefaciens* C58C$^1$ toward vir-Inducing Phenolic Compounds and Soluble Factors from Monocotyledonous and Dicotyledonous Plants", Journal of Bacteriology, vol. 170, pp. 4181-4187, Sep. 1988.
Bolton, et al., "Plant Phenolic Compounds Induce Expression of the *Agrobacteriurn tumefaciens* Loci Need for Virulence", Science, vol. 232, pp. 983-985, (1986).
Chalfie, et al., "Green Fluorescent Protein as a Marker for Gene Expression", Science, vol. 263, pp. 802-805, Feb. 1994.
Chilton and Que, "Targeted Integration of T-DNA into the Tobacco Genome at Double-Stranded Breaks: New Insights on the Mechanism of T-DNA Integration", Plant Physiology, vol. 133, pp. 956-965, Nov. 2003.
Choulika, et al., "Induction of Homologous Recombination in Mammalian Chromosomes by Using the I-*Sce*I System of *Saccharomyces cerevisiae*", Molecular and Cellular Biology, vol. 15, No. 4, pp. 1968-1973, Apr. 1995.
Colleaux, et al., "Recognition and Cleavage Site of the Intron-Encoded *omega* Transposase", Proc. Natl. Acad. Sci. USA, vol. 85. pp. 6022-6026, Aug. 1988.
Crameri, et al., "Improved Green Fluorescent Protein by Molecular Evolution Using DNA Shuffling", Nature Biotechnology, vol. 14, pp. 315-319, Mar. 1996.
De Block, et al., "Engineering Herbicide Resistance in Plants by Expression of a Detoxifying Enzyme", The EMBO Journal, vol. 6, No. 9, pp. 2513-2518, (1987).
Dujon et al., 95.6% Identical to SEQ ID No. 1, found in the Issued Patents Database, Sequence No. 2 from 5474896 (A), issued on Dec. 12, 1995.
Fennoy, et al., "Synonymous Codon Usage in *Zea mays* L. Nuclear genes is Varied by levels of C and G-ending Codons", Nucleic Acids Research, vol. 21, No. 23, pp. 5294-5300, (1993).
Guivarc'h, et al., "Localization of Target Cells and Improvement of *Agrabacterium*-mediated Transformation Efficiency by Direct Acetosyringone Pretreatment of Carrot Root Discs", Protoplasma, vol. 174, pp. 10-18, (1993).

(Continued)

*Primary Examiner* — Cathy Kingdon Worley
(74) *Attorney, Agent, or Firm* — Hunton & Williams LLP

(57) ABSTRACT

Methods and means are provided to improve targeted DNA insertion in plants using rare-cleaving "double stranded break" inducing enzymes. More specifically, the methods involve introducing the DNA that is to be inserted into the induced break into the plant cell via direct DNA delivery and incubating the plant cells in a plant phenolic compound prior to DNA delivery. Also provided are improved I-SceI encoding nucleotide sequences having a CG content of 50-60%.

13 Claims, 1 Drawing Sheet

(56) References Cited

OTHER PUBLICATIONS

Guo, et al., Protein Tolerance to Random Amino Acid Change, P.N.A.S., vol. 101(25), pp. 9205-9210, (2004).

Isalan, et al., "A Rapid, Generally Applicable Method to Engineer Zinc Fingers Illustrated by Targeting the HIV-1 Promoter", Nature Biotechnology, vol. 19, pp. 656-660, Jul. 2001.

Kalderon, et al., "A Short Amino Acid Sequence Able to Specify Nuclear Location", Cell, vol. 39, pp. 499-509, Dec. 1984.

Kawabe and Miyashita, "Patterns of Codon Usage Bias in Three Dicot and Four Monocot Plant Species", Genes Genet. Syst., vol. 78, pp. 343-352, (2003).

Krysiak, et al., "Generation of DNA Double-Strand Breaks and Inhibition of Somatic Embryogenesis by Tungsten Microparticles in Wheat", Plant Cell, Tissue and Organ Culture, vol. 58, pp. 163-170, (1999).

Kumar and Fladung "Controlling Transgene Integration in Plants", Trends in Plant Science, vol. 6, No. 4, pp. 155-159, Apr. 2001.

Lazar et al., "Transforming Growth Factor A: Mutation of Aspartic Acid 47 and Leucine 48 in Different Biological Activities", Molec. & Cell. Biol., vol. 8(3), pp. 1247-1252, (1988).

Liu, et al., "Design of Polydactyl Zinc-Finger Proteins for Unique Addressing within Complex Genomes", Proc. Natl. Acad. Sci. USA, vol. 94, pp. 5525-5530, May 1997.

Meyer, et al., "A New Petunia Flower Colour Generated by Transformation of a Mutant with a Maize Gene", Nature, vol. 330, p. 677-678, Dec. 1987.

Murray, et al., "Codon Usage in Plant Genes", Nucleic Acids Research, vol. 17, No. 2, pp. 477-498, Jan. 1989.

Paszkowski, et al., "Gene Targeting in Plants", The EMBO Journal, vol. 7, No. 13, pp. 4021-4026, (1988).

Perera, et al., "Cytosine Deaminase as a Negative Selective marker for *Arbidopsis*", Plant Molecular Biology, vol. 23, pp. 793-799, (1993).

Puchta, et al., "Homologous Recombination in Plant Cells is Enhanced by in vivo induction of Double Strand Breaks into DNA by a Site-Specific Endonuclease", Nucleic Acids Research, vol. 21, No. 22, pp. 5034-5040, (1993).

Puchta, et al., "Two Different but Related Mechanisms are Used in Plants for the Repair of Genomic Double-Strand Breaks by Homologous Recombination", Proc. Natl. Acad. Sci. USA, vol. 93, pp. 5055-5060, May 1996.

Raikhel, "Nuclear Targeting in Plants", Plant Physiol., vol. 100, pp. 1627-1632, (1992).

Salomon and Puchta, "Capture of Genomic and T-DNA Sequences during Double-Strand Break Repair in Somatic Plant Cells", The EMBO Journal, vol. 17, No. 20, pp. 6086-6095, (1998).

Srivastava and Ow, "Biolistic Mediated Site-Specific Integration in Rice", Molecular Breeding, vol. 8, pp. 345-350, (2001).

Stachel, et al., "Identification of the Signal Molecules Produced by Wounded Plant Cells that Activate T-DNA Transfer in *Agrobacterium tumefaciens*", Nature, vol. 318, pp. 624-629, Dec. 1985.

Stougaard, "Substrate-Dependent Negative Selection in Plants Using a Bacterial Cytosine Deaminase Gene", The Plant Journal, vol. 3, No. 5, pp. 755-761, (1993).

Tzfira, et al., "Site-Specific Integration of *Agrobacterium tumefaciens* T-DNA via Double-Stranded Intermediates", Plant Physiology, vol. 133, pp. 1011-1023, Nov. 2003.

Porteus et al. "Chimeric Nuclease Stimulate Gene Targeting in Human Cells", May 2, 2003, Science, 300:763.

Komari et al. "Advances in cereal gene transfer", Current Opinion in Plant Biology 1998, 1:161-165.

Hansen and Chilton, "'Agrolistic' transformation of plant cells: integration of T-strands generated in Planta", 1996, PNAS 93: 14978-14983.

Snyder et al., "Introduction of pathogen defense genes and a cytokine biosynthesis gene into Sugarbeet (*Beta vulgaris*) by Agrobacterium or particle bombardment", 1999, Plant Cell Reports 18(10): 829-834.

Taylor et al. "Microparticle Bombardment as a tool in Plant Sciences and Agricultural Biotechnology", 2002, DNA and Cell Biology 21(12): 963-977.

Decision of the Opposition Division for EP1689870, dated Dec. 5, 2011.

Rouet et al. "Expression of a site-specific endonuclease stimulates homologous recombination in mammalian cells", 1994, PNAS 91: 6064-6068.

Day et al. "Transgene integration into the same chromosome location can produce alleles that express at a predictable level, or alleles that are differentially silenced", 2000, Genes & Development 14: 2869-2880.

* cited by examiner

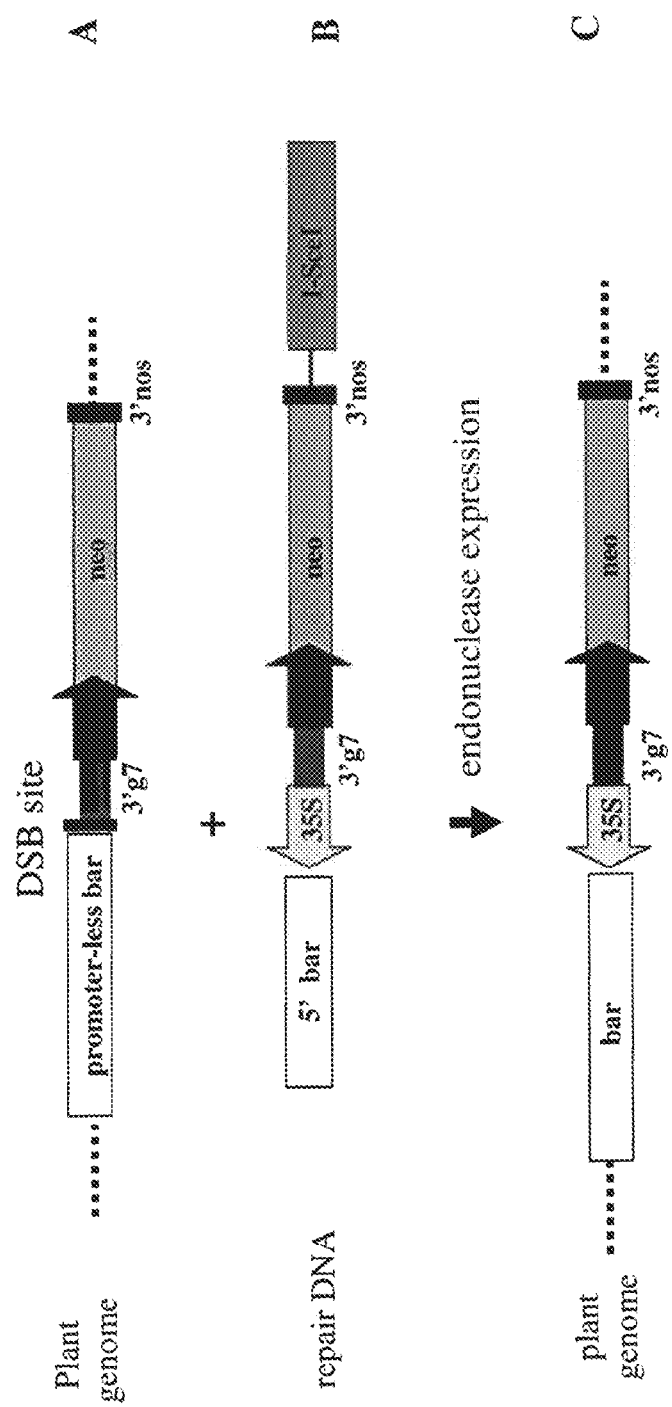

TARGETED DNA INSERTION IN PLANTS

CROSS-REFERENCE TO RELATED APPLICATIONS

This application is a divisional application of U.S. patent application Ser. No. 10/580,076, filed on May 18, 2006, issued as U.S. Pat. No. 7,598,365, which is a U.S. national stage application of International Application No. PCT/EP2004/013122, filed on Nov. 17, 2004, which claims the benefit of European Patent Application No. 03078700.6, filed on Nov. 18, 2003, the disclosures of each of which are herein incorporated by reference in their entireties.

FIELD OF THE INVENTION

The current invention relates to the field of molecular plant biology, more specific to the field of plant genome engineering. Methods are provided for the directed introduction of a foreign DNA fragment at a preselected insertion site in the genome of a plant. Plants containing the foreign DNA inserted at a particular site can now be obtained at a higher frequency and with greater accuracy than is possible with the currently available targeted DNA insertion methods. Moreover, in a large proportion of the resulting plants, the foreign DNA has only been inserted at the preselected insertion site, without the foreign DNA also having been inserted randomly at other locations in the plant's genome. The methods of the invention are thus an improvement, both quantitatively and qualitatively, over the prior art methods. Also provided are chimeric genes, plasmids, vectors and other means to be used in the methods of the invention.

BACKGROUND ART

The first generation of transgenic plants in the early 80's of last century by *Agrobacterium* mediated transformation technology, has spurred the development of other methods to introduce a foreign DNA of interest or a transgene into the genome of a plant, such as PEG mediated DNA uptake in protoplast, microprojectile bombardment, silicon whisker mediated transformation etc.

All the plant transformation methods, however, have in common that the transgenes incorporated in the plant genome are integrated in a random fashion and in unpredictable copy number. Frequently, the transgenes can be integrated in the form of repeats, either of the whole transgene or of parts thereof. Such a complex integration pattern may influence the expression level of the transgenes, e.g. by destruction of the transcribed RNA through posttranscriptional gene silencing mechanisms or by inducing methylation of the introduced DNA, thereby downregulating the transcriptional activity on the transgene. Also, the integration site per se can influence the level of expression of the transgene. The combination of these factors results in a wide variation in the level of expression of the transgenes or foreign DNA of interest among different transgenic plant cell and plant lines. Moreover, the integration of the foreign DNA of interest may have a disruptive effect on the region of the genome where the integration occurs, and can influence or disturb the normal function of that target region, thereby leading to, often undesirable, side-effects.

Therefore, whenever the effect of introduction of a particular foreign DNA into a plant is investigated, it is required that a large number of transgenic plant lines are generated and analysed in order to obtain significant results. Likewise, in the generation of transgenic crop plants, where a particular DNA of interest is introduced in plants to provide the transgenic plant with a desired, known phenotype, a large population of independently created transgenic plant lines or so-called events is created, to allow the selection of those plant lines with optimal expression of the transgenes, and with minimal, or no, side-effects on the overall phenotype of the transgenic plant. Particularly in this field, it would be advantageous if this trial-and-error process could be replaced by a more directed approach, in view of the burdensome regulatory requirements and high costs associated with the repeated field trials required for the elimination of the unwanted transgenic events. Furthermore, it will be clear that the possibility of targeted DNA insertion would also be beneficial in the process of so-called transgene stacking.

The need to control transgene integration in plants has been recognized early on, and several methods have been developed in an effort to meet this need (for a review see Kumar and Fladung, 2001, *Trends in Plant Science*, 6, pp 155-159). These methods mostly rely on homologous recombination-based transgene integration, a strategy which has been successfully applied in prokaryotes and lower eukaryotes (see e.g. EP0317509 or the corresponding publication by Paszkowski et al., 1988, *EMBO J.*, 7, pp 4021-4026). However, for plants, the predominant mechanism for transgene integration is based on illegitimate recombination which involves little homology between the recombining DNA strands. A major challenge in this area is therefore the detection of the rare homologous recombination events, which are masked by the far more efficient integration of the introduced foreign DNA via illegitimate recombination.

One way of solving this problem is by selecting against the integration events that have occurred by illegitimate recombination, such as exemplified in WO94/17176.

Another way of solving the problem is by activation of the target locus and/or repair or donor DNA through the induction of double stranded DNA breaks via rare-cutting endonucleases, such as I-SceI. This technique has been shown to increase the frequency of homologous recombination by at least two orders of magnitude using *Agrobacteria* to deliver the repair DNA to the plant cells (Puchta et al., 1996, *Proc. Natl. Acad. Sci. U.S.A.*, 93, pp 5055-5060; Chilton and Que, *Plant Physiol.*, 2003).

WO96/14408 describes an isolated DNA encoding the enzyme I-SceI. This DNA sequence can be incorporated in cloning and expression vectors, transformed cell lines and transgenic animals. The vectors are useful in gene mapping and site-directed insertion of genes.

WO00/46386 describes methods of modifying, repairing, attenuating and inactivating a gene or other chromosomal DNA in a cell through I-SceI double strand break. Also disclosed are methods of treating or prophylaxis of a genetic disease in an individual in need thereof. Further disclosed are chimeric restriction endonucleases.

However, there still remains a need for improving the frequency of targeted insertion of a foreign DNA in the genome of a eukaryotic cell, particularly in the genome of a plant cell. These and other problems are solved as described hereinafter in the different detailed embodiments of the invention, as well as in the claims.

SUMMARY OF THE INVENTION

In one embodiment, the invention provides a method for introducing a foreign DNA of interest, which may be flanked by a DNA region having at least 80% sequence identity to a DNA region flanking a preselected site, into a preselected site, such as an I-SceI site of a genome of a plant cell, such as a maize cell comprising the steps of
  (a) inducing a double stranded DNA break at the preselected site in the genome of the cell, e.g by introducing an I-SceI encoding gene;
  (b) introducing the foreign DNA of interest into the plant cell;
characterized in that the foreign DNA is delivered by direct DNA transfer which may be accomplished by bombardment of microprojectiles coated with the foreign DNA of interest. The I-SceI encoding gene can comprise a nucleotide sequence encoding the amino acid sequence of SEQ ID No 1, wherein said nucleotide sequence has a GC content of about 50% to about 60%, provided that
  i) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;
  ii) the nucleotide does not comprise a nucleotide sequence selected from the group consisting of CCAAT, ATTGG, GCAAT and ATTGC;
  iii) the nucleotide sequence does not comprise a sequence selected from the group consisting of ATTTA, AAGGT, AGGTA, GGTA or GCAGG;
  iv) the nucleotide sequence does not comprise a GC stretch consisting of 7 consecutive nucleotides selected from the group of G or C;
  v) the nucleotide sequence does not comprise a AT stretch consisting of 5 consecutive nucleotides selected from the group of A or T; and
  vi) the nucleotide sequence does not comprise the codons TTA, CTA, ATA, GTA, TCG, CCG, ACG and GCG. An example of such an I-SceI encoding gene comprises the nucleotide sequence of SEQ ID 4.
The plant cell may be incubated in a plant phenolic compound prior to step a).

In another embodiment, the invention relates to a method for introducing a foreign DNA of interest into a preselected site of a genome of a plant cell comprising the steps of
  (a) inducing a double stranded DNA break at the preselected site in the genome of the cell;
  (b) introducing the foreign DNA of interest into the plant cell;
    characterized in that the double stranded DNA break is introduced by a rare cutting endonuclease encoded by a nucleotide sequence wherein said nucleotide sequence has a GC content of about 50% to about 60%, provided that
    i) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;
    ii) the nucleotide does not comprise a nucleotide sequence selected from the group consisting of CCAAT, ATTGG, GCAAT and ATTGC;
    iii) the nucleotide sequence does not comprise a sequence selected from the group consisting of ATTTA, AAGGT, AGGTA, GGTA or GCAGG;
    iv) the nucleotide sequence does not comprise a GC stretch consisting of 7 consecutive nucleotides selected from the group of G or C;
    v) the nucleotide sequence does not comprise a AT stretch consisting of 5 consecutive nucleotides selected from the group of A or T; and
    vi) the nucleotide sequence does not comprise the codons TTA, CTA, ATA, GTA, TCG, CCG, ACG and GCG.

In yet another embodiment, the invention relates to a method for introducing a foreign DNA of interest into a preselected site of a genome of a plant cell comprising the steps of
  (a) inducing a double stranded DNA break at the preselected site in the genome of the cell;
  (b) introducing the foreign DNA of interest into the plant cell;
characterized in that prior to step a, the plant cells are incubated in a plant phenolic compound which may be selected from the group of acetosyringone (3,5-dimethoxy-4-hydroxyacetophenone), α-hydroxy-acetosyringone, sinapinic acid (3,5 dimethoxy-4-hydroxycinnamic acid), syringic acid (4-hydroxy-3,5 dimethoxybenzoic acid), ferulic acid (4-hydroxy-3-methoxycinnamic acid), catechol (1,2-dihydroxybenzene), p-hydroxybenzoic acid (4-hydroxybenzoic acid), β-resorcylic acid (2,4 dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) and vanillin (3-methoxy-4-hydroxybenzaldehyde).

The invention also provides an isolated DNA fragment comprising a nucleotide sequence encoding the amino acid sequence of SEQ ID No 1, wherein the nucleotide sequence has a GC content of about 50% to about 60%, provided that
  i) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;
  ii) the nucleotide does not comprise a nucleotide sequence selected from the group consisting of CCAAT, ATTGG, GCAAT and ATTGC;
  iii) the nucleotide sequence does not comprise a sequence selected from the group consisting of ATTTA, AAGGT, AGGTA, GGTA or GCAGG;
  iv) the nucleotide sequence does not comprise a GC stretch consisting of 7 consecutive nucleotides selected from the group of G or C;
  v) the nucleotide sequence does not comprise a AT stretch consisting of 5 consecutive nucleotides selected from the group of A or T; and
  vi) codons of said nucleotide sequence coding for leucine (Leu), isoleucine (Ile), valine (Val), serine (Ser), proline (Pro), threonine (Thr), alanine (Ala) do not comprise TA or GC duplets in positions 2 and 3 of said codons.

The invention also provides an isolated DNA sequence comprising the nucleotide sequence of SEQ ID No 4, as well as chimeric gene comprising the isolated DNA fragment according to the invention operably linked to a plant-expressible promoter and the use of such a chimeric gene to insert a foreign DNA into an I-SceI recognition site in the genome of a plant.

In yet another embodiment of the invention, a method is provided for introducing a foreign DNA of interest into a preselected site of a genome of a plant cell comprising the steps of
a) inducing a double stranded DNA break at the preselected site in the genome of the cell by a rare cutting endonuclease b) introducing the foreign DNA of interest into the plant cell; characterized in that said endonuclease comprises a nuclear localization signal.

BRIEF DESCRIPTION OF THE FIGURES

Table 1 represents the possible trinucleotide (codon) choices for a synthetic I-SceI coding region (see also the nucleotide sequence in SEQ ID No 2).

Table 2 represents preferred possible trinucleotide choices for a synthetic I-SceI coding region (see also the nucleotide sequence in SEQ ID No 3).

FIG. 1: Schematic representation of the target locus (A) and the repair DNA (B) used in the assay for homologous recombination mediated targeted DNA insertion. The target locus after recombination is also represented (C). DSB site: double stranded DNA break site; 3'g7:transcription termination and polyadenylation signal of *A. tumefaciens* gene 7; neo: plant expressible neomycin phosphotransferase; 35S: promoter of the CaMV 35S transcript; 5' bar: DNA region encoding the amino terminal portion of the phosphinotricin acetyltransferase; 3'nos: transcription termination and polyadenylation signal of *A. tumefaciens* nopaline synthetase gene; Pnos: promoter of the nopaline synthetase gene of *A. tumefaciens*; 3'ocs: 3' transcription termination and polyadenylation signal of the octopine synthetase gene of *A. tumefaciens*.

DETAILED DESCRIPTION

The current invention is based on the following findings:
a) Introduction into the plant cells of the foreign DNA to be inserted via direct DNA transfer, particularly microprojectile bombardment, unexpectedly increased the frequency of targeted insertion events. All of the obtained insertion events were targeted DNA insertion events, which occurred at the site of the induced double stranded DNA break. Moreover all of these targeted insertion events appeared to be exact recombination events between the provided sequence homology flanking the double stranded DNA break. Only about half of these events had an additional insertion of the foreign DNA at a site different from the site of the induced double stranded DNA break.
b) Induction of the double stranded DNA break by transient expression of a rare-cutting double stranded break inducing endonuclease, such as I-SceI, encoded by chimeric gene comprising a synthetic coding region for a rare-cutting endonuclease such as I-SceI designed according to a preselected set of rules surprisingly increased the quality of the resulting targeted DNA insertion events (i.e. the frequency of perfectly targeted DNA insertion events). Furthermore, the endonuclease had been equipped with a nuclear localization signal.
c) Preincubation of the target cells in a plant phenolic compound, such as acetosyringone, further increased the frequency of targeted insertion at double stranded DNA breaks induced in the genome of a plant cell.

Any of the above findings, either alone or in combination, improves the frequency with which homologous recombination based targeted insertion events can be obtained, as well as the quality of the recovered events.

Thus, in one aspect, the invention relates to a method for introducing a foreign DNA of interest into a preselected site of a genome of a plant cell comprising the steps of
  (a) inducing a double stranded DNA break at the preselected site in the genome of the cell;
  (b) introducing the foreign DNA of interest into the plant cell;
    characterized in that the foreign DNA is delivered by direct DNA transfer.

As used herein "direct DNA transfer" is any method of DNA introduction into plant cells which does not involve the use of natural *Agrobacterium* spp. which is capable of introducing DNA into plant cells. This includes methods well known in the art such as introduction of DNA by electroporation into protoplasts, introduction of DNA by electroporation into intact plant cells or partially degraded tissues or plant cells, introduction of DNA through the action of agents such as PEG and the like, into protoplasts, and particularly bombardment with DNA coated microprojectiles. Introduction of DNA by direct transfer into plant cells differs from *Agrobacterium*-mediated DNA introduction at least in that double stranded DNA enters the plant cell, in that the entering DNA is not coated with any protein, and in that the amount of DNA entering the plant cell may be considerably greater. Furthermore, DNA introduced by direct transfer methods, such as the introduced chimeric gene encoding a double stranded DNA break inducing endonuclease, may be more amenable to transcription, resulting in a better timing of the induction of the double stranded DNA break. Although not intending to limit the invention to a particular mode of action, it is thought that the efficient homology-recombination-based insertion of repair DNA or foreign DNA in the genome of a plant cell may be due to a combination of any of these parameters.

Conveniently, the double stranded DNA break may be induced at the preselected site by transient expression after introduction of a plant-expressible gene encoding a rare cleaving double stranded break inducing enzyme. As set forth elsewhere in this document, I-SceI may be used for that purpose to introduce a foreign DNA at an I-SceI recognition site. However, it will be immediately clear to the person skilled in the art that also other double stranded break inducing enzymes can be used to insert the foreign DNA at their respective recognition sites. A list of rare cleaving DSB inducing enzymes and their respective recognition sites is provided in Table I of WO 03/004659 (pages 17 to 20) (incorporated herein by reference). Furthermore, methods are available to design custom-tailored rare-cleaving endonucleases that recognize basically any target nucleotide sequence of choice. Such methods have been described e.g. in WO 03/080809, WO94/18313 or WO95/09233 and in Isalan et al., 2001, *Nature Biotechnology* 19, 656-660; Liu et al. 1997, *Proc. Natl. Acad. Sci. USA* 94, 5525-5530.)

Thus, as used herein "a preselected site" indicates a particular nucleotide sequence in the plant nuclear genome at which location it is desired to insert the foreign DNA. A person skilled in the art would be perfectly able to either choose a double stranded DNA break inducing ("DSBI") enzyme recognizing the selected target nucleotide sequence or engineer such a DSBI endonuclease. Alternatively, a DSBI endonuclease recognition site may be introduced into the plant genome using any conventional transformation method or by conventional breeding using a plant line having a DSBI endonuclease recognition site in its genome, and any desired foreign DNA may afterwards be introduced into that previously introduced preselected target site.

The double stranded DNA break may be induced conveniently by transient introduction of a plant-expressible chimeric gene comprising a plant-expressible promoter region operably linked to a DNA region encoding a double stranded break inducing enzyme. The DNA region encoding a double stranded break inducing enzyme may be a synthetic DNA region, such as but not limited to, a synthetic DNA region whereby the codons are chosen according to the design scheme as described elsewhere in this application for I-SceI encoding regions.

The double stranded break inducing enzyme may comprise, but need not comprise, a nuclear localization signal (NLS) [Raikhel, *Plant Physiol.* 100: 1627-1632 (1992) and references therein], such as the NLS of SV40 large T-antigen [Kalderon et al. *Cell* 39: 499-509 (1984)]. The nuclear localization signal may be located anywhere in the protein, but is conveniently located at the N-terminal end of the protein. The nuclear localization signal may replace one or more of the amino acids of the double stranded break inducing enzyme.

As used herein "foreign DNA of interest" indicates any DNA fragment which one may want to introduce at the preselected site. Although it is not strictly required, the foreign DNA of interest may be flanked by at least one nucleotide sequence region having homology to a DNA region flanking the preselected site. The foreign DNA of interest may be flanked at both sites by DNA regions having homology to both DNA regions flanking the preselected site. Thus the repair DNA molecule(s) introduced into the plant cell may comprise a foreign DNA flanked by one or two flanking sequences having homology to the DNA regions respectively upstream or downstream of the preselected site. This allows to better control the insertion of the foreign DNA. Indeed, integration by homologous recombination will allow precise joining of the foreign DNA fragment to the plant nuclear genome up to the nucleotide level.

The flanking nucleotide sequences may vary in length, and should be at least about 10 nucleotides in length. However, the flanking region may be as long as is practically possible (e.g. up to about 100-150 kb such as complete bacterial artificial chromosomes (BACs)). Preferably, the flanking region will be about 50 bp to about 2000 bp. Moreover, the regions flanking the foreign DNA of interest need not be identical to the DNA regions flanking the preselected site and may have between about 80% to about 100% sequence identity, preferably about 95% to about 100% sequence identity with the DNA regions flanking the preselected site. The longer the flanking region, the less stringent the requirement for homology. Furthermore, it is preferred that the sequence identity is as high as practically possible in the vicinity of the location of exact insertion of the foreign DNA.

Moreover, the regions flanking the foreign DNA of interest need not have homology to the regions immediately flanking the preselected site, but may have homology to a DNA region of the nuclear genome further remote from that preselected site. Insertion of the foreign DNA will then result in a removal of the target DNA between the preselected insertion site and the DNA region of homology. In other words, the target DNA located between the homology regions will be substituted for the foreign DNA of interest.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

In another aspect, the invention relates to a modified I-SceI encoding DNA fragment, and the use thereof to efficiently introduce a foreign DNA of interest into a preselected site of a genome of a plant cell, whereby the modified I-SceI encoding DNA fragment has a nucleotide sequence which has been designed to fulfill the following criteria:

a) the nucleotide sequence encodes a functional I-SceI endonuclease, such as an I-SceI endonuclease having the amino acid sequence as provided in SEQ ID No 1.

b) the nucleotide sequence has a GC content of about 50% to about 60% c) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;

d) the nucleotide does not comprise a nucleotide sequence selected from the group consisting of CCAAT, ATTGG, GCAAT and ATTGC;

e) the nucleotide sequence does not comprise a sequence selected from the group consisting of ATTTA, AAGGT, AGGTA, GGTA or GCAGG;

f) the nucleotide sequence does not comprise a GC stretch consisting of 7 consecutive nucleotides selected from the group of G or C;

g) the nucleotide sequence does not comprise a GC stretch consisting of 5 consecutive nucleotides selected from the group of A or T; and h) the nucleotide sequence does not comprise codons coding for Leu, Ile, Val, Ser, Pro, Thr, Ala that comprise TA or CG duplets in positions 2 and 3 (i.e. the nucleotide sequence does not comprise the codons TTA, CTA, ATA, GTA, TCG, CCG, ACG and GCG).

I-SceI is a site-specific endonuclease, responsible for intron mobility in mitochondria in *Saccharomyces cerevisea*. The enzyme is encoded by the optional intron Sc LSU.1 of the 21S rRNA gene and initiates a double stranded DNA break at the intron insertion site generating a 4 bp staggered cut with 3'OH overhangs. The recognition site of I-SceI endonuclease extends over an 18 bp non-symmetrical sequence (Colleaux et al. 1988 *Proc. Natl. Acad. Sci. USA* 85: 6022-6026). The amino acid sequence for I-SceI and a universal code equivalent of the mitochondrial I-SceI gene have been provided by e.g. WO 96/14408.

WO 96/14408 discloses that the following variants of I-SceI protein are still functional:

positions 1 to 10 can be deleted
position 36: Gly (G) is tolerated
position 40: Met (M) or Val (V) are tolerated
position 41: Ser (S) or Asn (N) are tolerated
position 43: Ala (A) is tolerated
position 46: Val (V) or N (Asn) are tolerated
position 91: Ala (A) is tolerated
positions 123 and 156: Leu (L) is tolerated
position 223: Ala (A) and Ser (S) are tolerated and synthetic nucleotide sequences encoding such variant I-SceI enzymes can also be designed and used in accordance with the current invention.

A nucleotide sequence encoding the amino acid sequence of I-SceI, wherein the amino-terminally located 4 amino acids have been replaced by a nuclear localization signal (SEQ ID 1) thus consist of 244 trinucleotides which can be represented as R1 through R244. For each of these positions between 1 and 6 possible choices of trinucleotides encoding the same amino acid are possible. Table 1 sets forth the possible choices for the trinucleotides encoding the amino acid sequence of SEQ ID 1 and provides for the structural requirements (either conditional or absolute) which allow to avoid inclusion into the synthetic DNA sequence the above mentioned "forbidden nucleotide sequences". Also provided is the nucleotide sequence of the contiguous trinucleotides in UIPAC code.

As used herein, the symbols of the UIPAC code have their usual meaning i.e. N=A or C or G or T; R=A or G; Y=C or T; B=C or G or T (not A); V=A or C or G (not T); D=A or G or T (not C); H=A or C or T (not G); K=G or T; M=A or C; S=G or C; W=A or T.

Thus in one embodiment of the invention, an isolated synthetic DNA fragment is provided which comprises a nucleotide sequence as set forth in SEQ ID No 2, wherein the codons are chosen among the choices provided in such a way as to obtain a nucleotide sequence with an overall GC content of about 50% to about 60%, preferably about 54%-55% provided that the nucleotide sequence from position 28 to position 30 is not AAG; if the nucleotide sequence from position 34 to position 36 is AAT then the nucleotide sequence from position 37 to position 39 is not ATT or ATA; if the nucleotide sequence form position 34 to position 36 is AAC then the nucleotide sequence from position 37 to position 39 is not ATT simultaneously with the nucleotide sequence from position 40 to position 42 being AAA; if the nucleotide sequence from position 34 to position 36 is AAC then the nucleotide sequence from position 37 to position 39 is not ATA; if the nucleotide sequence from position 37 to position 39 is ATT or ATA then the nucleotide sequence from position 40 to 42 is not AAA; the nucleotide sequence from position 49 to position 51 is not CAA; the nucleotide sequence from position 52 to position 54 is not GTA; the codons from the nucleotide sequence from position 58 to position 63 are chosen according to the choices provided in such a way that the resulting nucleotide sequence does not comprise ATTTA; if the nucleotide sequence from position 67 to position 69 is CCC then the nucleotide sequence from position 70 to position 72 is not AAT; if the nucleotide sequence from position 76 to position 78 is AAA then the nucleotide sequence from position 79 to position 81 is not TTG simultaneously with the nucleotide sequence from position 82 to 84 being CTN; if the nucleotide sequence from position 79 to position 81 is TTA or CTA then the nucleotide sequence from position 82 to position 84 is not TTA; the nucleotide sequence from position 88 to position 90 is not GAA; if the nucleotide sequence from position 91 to position 93 is TAT, then the nucleotide sequence from position 94 to position 96 is not AAA; if the nucleotide sequence from position from position 97 to position 99 is TCC or TCG or AGC then the nucleotide sequence from position 100 to 102 is not CCA simultaneously with the nucleotide sequence from position 103 to 105 being TTR; it the nucleotide sequence from position 100 to 102 is CAA then the nucleotide sequence from position 103 to 105 is not TTA; if the nucleotide sequence from position 109 to position 111 is GAA then the nucleotide sequence from 112 to 114 is not TTA; if the nucleotide sequence from position 115 to 117 is AAT then the nucleotide sequence from position 118 to position 120 is not ATT or ATA; if the nucleotide sequence from position 121 to 123 is GAG then the nucleotide sequence from position 124 to position 126; the nucleotide sequence from position 133 to 135 is not GCA; the nucleotide sequence from position 139 to position 141 is not ATT; if the nucleotide sequence from position 142 to position 144 is GGA then the nucleotide sequence from position 145 to position 147 is not TTA; if the nucleotide sequence from position 145 to position 147 is TTA then the nucleotide sequence from position 148 to position 150 is not ATA simultaneously with the nucleotide sequence from position 151 to 153 being TTR; if the nucleotide sequence from position 145 to position 147 is CTA then the nucleotide sequence from position 148 to position 150 is not ATA simultaneously with the nucleotide sequence from position 151 to 153 being TTR; if the nucleotide sequence from position 148 to position 150 is ATA then the nucleotide sequence from position 151 to position 153 is not CTA or TTG; if the nucleotide sequence from position 160 to position 162 is GCA then the nucleotide sequence from position 163 to position 165 is not TAC; if the nucleotide sequence from position 163 to position 165 is TAT then the nucleotide sequence from position 166 to position 168 is not ATA simultaneously with the nucleotide sequence from position 169 to position 171 being AGR; the codons from the nucleotide sequence from position 172 to position 177 are chosen according to the choices provided in such a way that the resulting nucleotide sequence does not comprise GCAGG; the codons from the nucleotide sequence from position 178 to position 186 are chosen according to the choices provided in such a way that the resulting nucleotide sequence does not comprise AGGTA; if the nucleotide sequence from position 193 to position 195 is TAT, then the nucleotide sequence from position 196 to position 198 is not TGC; the nucleotide sequence from position 202 to position 204 is not CAA; the nucleotide sequence from position 217 to position 219 is not AAT; if the nucleotide sequence from position 220 to position 222 is AAA then the nucleotide sequence from position 223 to position 225 is not GCA; if the nucleotide sequence from position 223 to position 225 is GCA then the nucleotide sequence from position 226 to position 228 is not TAC; if the nucleotide sequence from position 253 to position 255 is GAC, then the nucleotide sequence from position 256 to position 258 is not CAA; if the nucleotide sequence from position 277 to position 279 is CAT, then the nucleotide sequence from position 280 to position 282 is not AAA; the codons from the nucleotide sequence from position 298 to position 303 are chosen according to the choices provided in such a way that the resulting nucleotide sequence does not comprise ATTTA; if the nucleotide sequence from position 304 to position 306 is GGC then the nucleotide sequence from position 307 to position 309 is not AAT; the codons from the nucleotide sequence from position 307 to position 312 are chosen according to the choices provided in such a way that the resulting nucleotide sequence does not comprise ATTTA; the codons from the nucleotide sequence from position 334 to position 342 are chosen according to the choices provided in such a way that the resulting nucleotide sequence does not comprise ATTTA; if the nucleotide sequence from position 340 to position 342 is AAG then the nucleotide sequence from position 343 to 345 is not CAT; if the nucleotide position from position 346 to position 348 is CAA then the nucleotide sequence from position 349 to position 351 is not GCA; the codons from the nucleotide sequence from position 349 to position 357 are chosen according to the choices provided in such a way that the resulting nucleotide sequence does not comprise ATTTA; the nucleotide sequence from position 355 to position 357 is not AAT; if the nucleotide sequence from position 358 to position 360 is AAA then the nucleotide sequence from position 361 to 363 is not TTG; if the nucleotide sequence from position 364 to position 366 is GCC then the nucleotide sequence from position 367 to position 369 is not AAT; the codons from the nucleotide sequence from position 367 to position 378 are chosen according to the choices provided in such a way that the resulting nucleotide sequence does not comprise ATTTA; if the nucleotide sequence from position 382 to position 384 is AAT then the nucleotide sequence from position 385 to position 387 is not AAT; the nucleotide sequence from position 385 to position 387 is not AAT; if the nucleotide sequence from position 400 to 402 is CCC, then the nucleotide sequence from position 403 to 405 is not AAT; if the nucleotide sequence from position 403 to 405 is AAT, then the nucleotide sequence from position 406 to 408 is not AAT; the codons from the nucleotide sequence from position 406 to position 411 are chosen according to the choices provided in such a way that the resulting nucleotide sequence does not comprise ATTTA; the codons from the nucleotide sequence from position 421 to position 426 are chosen according to the choices provided in such a way that the resulting nucleotide sequence does not comprise ATTA; the nucleotide sequence from position 430 to position 432 is not CCA; if the nucleotide sequence from position 436 to position 438 is TCA then the nucleotide sequence from position 439 to position 441 is not TTG; the nucleotide sequence from position 445 to position 447 is not TAT; the nucleotide sequence from position 481 to 483 is not AAT; if the nucleotide sequence from position 484 to position 486 is AAA, then the nucleotide sequence from position 487 to position 489 is not AAT simultaneously with the nucleotide sequence from position 490 to position 492 being AGY; if the nucleotide sequence from position 490 to position 492 is TCA, then the nucleotide sequence from position 493 to position 495 is not ACC simultaneously with the nucleotide sequence from position 496 to 498 being AAY; if the nucleotide sequence from position 493 to position 495 is ACC, then the nucleotide sequence from position 496 to 498 is not AAT; the nucleotide sequence from position 496 to position 498 is not AAT; if the nucleotide sequence from position 499 to position 501 is AAA then the nucleotide sequence from position 502 to position 504 is not TCA or AGC; if the nucleotide sequence from position 508 to position 510 is GTA, then the nucleotide sequence from position 511 to 513 is not TTA; if the nucleotide sequence from position 514 to position 516 is AAT then the nucleotide sequence from position 517 to position 519 is not ACA; if the nucleotide sequence from position 517 to position 519 is ACC or ACG, then the nucleotide sequence from position 520 to position 522 is not CAA simultaneously with the nucleotide sequence from position 523 to position 525 being TCN; the codons from the nucleotide sequence from position 523 to position 531 are chosen according to the choices provided in such a way that the resulting nucleotide sequence does not comprise ATTTA; if the nucleotide sequence from position 544 to position 546 is GAA then the nucleotide sequence from position 547 to position 549 is not TAT, simultaneously with the nucleotide sequence from position 550 to position 552 being TTR; the codons from the nucleotide sequence from position 547 to position 552 are chosen according to the choices provided in such a way that the resulting nucleotide sequence does not comprise ATTTA; if the nucleotide sequence from position 559 to position 561 is GGA then the nucleotide sequence from position 562 to position 564 is not TTG simultaneously with the nucleotide sequence from position 565 to 567 being CGN; if the nucleotide sequence from position 565 to position 567 is CGC then the nucleotide sequence from position 568 to position 570 is not AAT; the nucleotide sequence from position 568 to position 570 is not AAT; if the nucleotide sequence from position 574 to position 576 is TTC then the nucleotide sequence from position 577 to position 579 is not CAA simultaneously with the nucleotide sequence from position 580 to position 582 being TTR; if the nucleotide sequence from position 577 to position 579 is CAA then the nucleotide sequence from position 580 to position 582 is not TTA; if the nucleotide sequence from position 583 to position 585 is AAT the nucleotide sequence from position 586 to 588 is not TGC; the nucleotide sequence from position 595 to position 597 is not AAA; if the nucleotide sequence from position 598 to position 600 is ATT then the nucleotide sequence from position 601 to position 603 is not AAT; the nucleotide sequence from position 598 to position 600 is not ATA; the nucleotide sequence from position 601 to position 603 is not AAT; if the nucleotide sequence from position 604 to position 606 is AAA then the nucleotide sequence from position 607 to position 609 is not AAT; the nucleotide sequence from position 607 to position 609 is not AAT; the nucleotide sequence from position 613 to position 615 is not CCA; if the nucleotide sequence from position 613 to position 615 is CCG, then the nucleotide sequence from position 616 to position 618 is not ATA; if the nucleotide sequence from position 616 to the nucleotide at position 618 is ATA, then the nucleotide sequence from position 619 to 621 is not ATA; if the nucleotide sequence from position 619 to position 621 is ATA, then the nucleotide sequence from position 622 to position 624 is not TAC; the nucleotide sequence from position 619 to position 621 is not ATT; the codons from the nucleotide sequence from position 640 to position 645 are chosen according to the choices provided in such a way that the resulting nucleotide sequence does not comprise ATTTA; if the nucleotide sequence from position 643 to position 645 is TTA then the nucleotide sequence from position 646 to position 648 is not ATA; if the nucleotide sequence from position 643 to position 645 is CTA then the nucleotide sequence from position 646 to position 648 is not ATA; the codons from the nucleotide sequence from position 655 to position 660 are chosen according to the choices provided in such a way that the resulting nucleotide sequence does not comprise ATTTA; if the nucleotide sequence from position 658 to 660 is TTA or CTA then the nucleotide sequence from position 661 to position 663 is not ATT or ATC; the nucleotide sequence from position 661 to position 663 is not ATA; if the nucleotide sequence from position 661 to position 663 is ATT then the nucleotide sequence from position 664 to position 666 is not AAA; the codons from the nucleotide sequence from position 670 to position 675 are chosen according to the choices provided in such a way that the resulting nucleotide sequence does not comprise ATTTA; if the nucleotide sequence from position 691 to position 693 is TAT then the nucleotide sequence from position 694 to position 696 is not AAA; if the nucleotide sequence from position 694 to position 696 is AAA then the nucleotide sequence from position 697 to position 699 is not TTG; if the nucleotide sequence from position 700 to position 702 is CCC then the nucleotide sequence from position 703 to position 705 is not AAT; if the nucleotide sequence from position 703 to position 705 is AAT then the nucleotide sequence from position 706 to position 708 is not ACA or ACT; if the nucleotide sequence from position 706 to position 708 is ACA then the nucleotide sequence from position 709 to 711 is not ATA simultaneously with the nucleotide sequence from position 712 to position 714 being AGY; the nucleotide sequence does not comprise the codons TTA, CTA, ATA, GTA, TCG, CCG, ACG and GCG; said nucleotide sequence does not comprise a GC stretch consisting of 7 consecutive nucleotides selected from the group of G or C; and the nucleotide sequence does not comprise a AT stretch consisting of 5 consecutive nucleotides selected from the group of A or T.

A preferred group of synthetic nucleotide sequences is set forth in Table 2 and corresponds to an isolated synthetic DNA fragment is provided which comprises a nucleotide sequence as set forth in SEQ ID No 3, wherein the codons are chosen among the choices provided in such a way as to obtain a nucleotide sequence with an overall GC content of about 50% to about 60%, preferably about 54%-55% provided that if the nucleotide sequence from position 121 to position 123 is GAG then the nucleotide sequence from position 124 to 126 is not CAA; if the nucleotide sequence from position 253 to position 255 is GAC then the nucleotide sequence from position 256 to 258 is not CAA; if the nucleotide sequence from position 277 to position 279 is CAT then the nucleotide sequence from position 280 to 282 is not AAA; if the nucleotide sequence from position 340 to position 342 is AAG then the nucleotide sequence from position 343 to position 345 is not CAT; if the nucleotide sequence from position 490 to position 492 is TCA then the nucleotide sequence from position 493 to position 495 is not ACC; if the nucleotide sequence from position 499 to position 501 is AAA then the nucleotide sequence from position 502 to 504 is not TCA or AGC; if the nucleotide sequence from position 517 to position 519 is ACC then the nucleotide sequence from position 520 to position 522 is not CAA simultaneous with the nucleotide sequence from position 523 to 525 being TCN; if the nucleotide sequence from position 661 to position 663 is ATT then the nucleotide sequence from position 664 to position 666 is not AAA; the codons from the nucleotide sequence from position 7 to position 15 are chosen according to the choices provided in such a way that the resulting nucleotide sequence does not comprise a stretch of seven contiguous nucleotides from the group of G or C; the codons from the nucleotide sequence from position 61 to position 69 are chosen according to the choices provided in such a way that the resulting nucleotide sequence does not comprise a stretch of seven contiguous nucleotides from the group of G or C; the codons from the nucleotide sequence from position 130 to position 138 are chosen according to the choices provided in such a way that the resulting nucleotide sequence does not comprise a stretch of seven contiguous nucleotides from the group of G or C; the codons from the nucleotide sequence from position 268 to position 279 are chosen according to the choices provided in such a way that the resulting nucleotide sequence does not comprise a stretch of seven contiguous nucleotides from the group of G or C; the codons from the nucleotide sequence from position 322 to position 333 are chosen according to the choices provided in such a way that the resulting nucleotide sequence does not comprise a stretch of seven contiguous nucleotides from the group of G or C; the codons from the nucleotide sequence from position 460 to position 468 are chosen according to the choices provided in such a way that the resulting nucleotide sequence does not comprise a stretch of seven contiguous nucleotides from the group of G or C; the codons from the nucleotide sequence from position 13 to position 27 are chosen according to the choices provided in such a way that the resulting nucleotide sequence does not comprise a stretch of five contiguous nucleotides from the group of A or T; the codons from the nucleotide sequence from position 37 to position 48 are chosen according to the choices provided in such a way that the resulting nucleotide sequence does not comprise a stretch of five contiguous nucleotides from the group of A or T; the codons from the nucleotide sequence from position 184 to position 192 are chosen according to the choices provided in such a way that the resulting nucleotide sequence does not comprise a stretch of five contiguous nucleotides from the group of A or T; the codons from the nucleotide sequence from position 214 to position 219 are chosen according to the choices provided in such a way that the resulting nucleotide sequence does not comprise a stretch of five contiguous nucleotides from the group of A or T; the codons from the nucleotide sequence from position 277 to position 285 are chosen according to the choices provided in such a way that the resulting nucleotide sequence does not comprise a stretch of five contiguous nucleotides from the group of A or T; and the codons from the nucleotide sequence from position 388 to position 396 are chosen according to the choices provided in such a way that the resulting nucleotide sequence does not comprise a stretch of five contiguous nucleotides from the group of A or T; the codons from the nucleotide sequence from position 466 to position 474 are chosen according to the choices provided in such a way that the resulting nucleotide sequence does not comprise a stretch of five contiguous nucleotides from the group of A or T; the codons from the nucleotide sequence from position 484 to position 489 are chosen according to the choices provided in such a way that the resulting nucleotide sequence does not comprise a stretch of five contiguous nucleotides from the group of A or T; the codons from the nucleotide sequence from position 571 to position 576 are chosen according to the choices provided in such a way that the resulting nucleotide sequence does not comprise a stretch of five contiguous nucleotides from the group of A or T; the codons from the nucleotide sequence from position 598 to position 603 are chosen according to the choices provided in such a way that the resulting nucleotide sequence does not comprise a stretch of five contiguous nucleotides from the group of A or T; the codons from the nucleotide sequence from position 604 to position 609 are chosen according to the choices provided in such a way that the resulting nucleotide sequence does not comprise a stretch of five contiguous nucleotides from the group of A or T; the codons from the nucleotide sequence from position 613 to position 621 are chosen according to the choices provided in such a way that the resulting nucleotide sequence does not comprise a stretch of five contiguous nucleotides from the group of A or T; the codons from the nucleotide sequence from position 646 to position 651 are chosen according to the choices provided in such a way that the resulting nucleotide sequence does not comprise a stretch of five contiguous nucleotides from the group of A or T; the codons from the nucleotide sequence from position 661 to position 666 are chosen according to the choices provided in such a way that the resulting nucleotide sequence does not comprise a stretch of five contiguous nucleotides from the group of A or T; and the codons from the nucleotide sequence from position 706 to position 714 are chosen according to the choices provided in such a way that the resulting nucleotide sequence does not comprise a stretch of five contiguous nucleotides from the group of A or T.

The nucleotide sequence of SEQ ID No 4 is an example of such a synthetic nucleotide sequence encoding an I-SceI endonuclease which does no longer contain any of the nucleotide sequences or codons to be avoided. However, it will be clear that a person skilled in the art can readily obtain a similar sequence encoding I-SceI by replacing one or more (between two to twenty) of the nucleotides to be chosen for any of the alternatives provided in the nucleotide sequence of SEQ ID 3 (excluding any of the forbidden combinations described in the preceding paragraph) and use it to obtain a similar effect.

For expression in plant cell, the synthetic DNA fragments encoding I-SceI may be operably linked to a plant expressible promoter in order to obtain a plant expressible chimeric gene.

A person skilled in the art will immediately recognize that for this aspect of the invention, it is not required that the repair DNA and/or the DSBI endonuclease encoding DNA are introduced into the plant cell by direct DNA transfer methods, but that the DNA may thus also be introduced into plant cells by *Agrobacterium*-mediated transformation methods as are available in the art.

In yet another aspect, the invention relates to a method for introducing a foreign DNA of interest into a preselected site of a genome of a plant cell comprising the steps of
(a) inducing a double stranded break at the preselected site in the genome of the cell;
(b) introducing the foreign DNA of interest into the plant cell;
characterized in that prior to step (a), the plant cells are incubated in a plant phenolic compound.

"Plant phenolic compounds" or "plant phenolics" suitable for the invention are those substituted phenolic molecules which are capable to induce a positive chemotactic response, particularly those who are capable to induce increased vir gene expression in a Ti-plasmid containing *Agrobacterium* sp., particularly a Ti-plasmid containing *Agrobacterium tumefaciens*. Methods to measure chemotactic response towards plant phenolic compounds have been described by Ashby et al. (1988 *J. Bacteriol.* 170: 4181-4187) and methods to measure induction of vir gene expression are also well known (Stachel et al., 1985 *Nature* 318: 624-629; Bolton et al. 1986 *Science* 232: 983-985). Preferred plant phenolic compounds are those found in wound exudates of plant cells. One of the best known plant phenolic compounds is acetosyringone, which is present in a number of wounded and intact cells of various plants, albeit it in different concentrations. However, acetosyringone (3,5-dimethoxy-4-hydroxyacetophenone) is not the only plant phenolic which can induce the expression of vir genes. Other examples are α-hydroxyacetosyringone, sinapinic acid (3,5 dimethoxy-4-hydroxycinnamic acid), syringic acid (4-hydroxy-3,5 dimethoxybenzoic acid), ferulic acid (4-hydroxy-3-methoxycinnamic acid), catechol (1,2-dihydroxybenzene), p-hydroxybenzoic acid (4-hydroxybenzoic acid), β-resorcylic acid (2,4 dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) and vanillin (3-methoxy-4-hydroxybenzaldehyde). As used herein, the mentioned molecules are referred to as plant phenolic compounds. Plant phenolic compounds can be added to the plant culture medium either alone or in combination with other plant phenolic compounds. Although not intending to limit the invention to a particular mode of action, it is thought that the apparent stimulating effect of these plant phenolics on cell division (and thus also genome replication) may be enhancing targeted insertion of foreign DNA.

Plant cells are preferably incubated in plant phenolic compound for about one week, although it is expected incubation for about one or two days in or on a plant phenolic compound will be sufficient. Plant cells should be incubated for a time sufficient to stimulate cell division. According to Guivarc'h et al. (1993, *Protoplasma* 174: 10-18) such effect may already be obtained by incubation of plant cells for as little as 10 minutes.

The above mentioned improved methods for homologous recombination based targeted DNA insertion may also be applied to improve the quality of the transgenic plant cells and plants obtained by direct DNA transfer methods, particularly by microprojectile bombardment. It is well known in the art that introduction of DNA by microprojectile bombardment frequently leads to complex integration patterns of the introduced DNA (integration of multiple copies of the foreign DNA of interest, either complete or partial, generation of repeat structures). Nevertheless, some plant genotypes or varieties may be more amenable to transformation using microprojectile bombardment than to transformation using e.g. *Agrobacterium tumefaciens*. It would thus be advantageous if the quality of the transgenic plant cells or plants obtained through microprojectile bombardment could be improved, i.e. if the pattern of integration of the foreign DNA could be influenced to be simpler.

The above mentioned finding that introduction of foreign DNA through microprojectile bombardment in the presence of an induced double stranded DNA break in the nuclear genome, whereby the foreign DNA has homology to the sequences flanking the double stranded DNA break frequently (about 50% of the obtained events) leads to simple integration patterns (single copy insertion in a predictable way and no insertion of additional fragments of the foreign DNA) provides the basis for a method of simplifying the complexity of insertion of foreign DNA in the nuclear genome of plant cells.

Thus the invention also relates to a method of producing a transgenic plant by microprojectile bombardment comprising the steps of
(a) inducing a double stranded DNA break at a preselected site in the genome of a cell a plant, in accordance with the methods described elsewhere in this document or available in the art; and
(b) introducing the foreign DNA of interest into the plant cell by microprojectile bombardment wherein said foreign DNA of interest is flanked by two DNA regions having at least 80% sequence identity to the DNA regions flanking the preselected site in the genome of the plant.

A significant portion of the transgenic plant population thus obtained will have a simple integration pattern of the foreign DNA in the genome of the plant cells, more particularly a significant portion of the transgenic plants will only have a one copy insertion of the foreign DNA, exactly between the two DNA regions flanking the preselected site in the genome of the plant. This portion is higher than the population of transgenic plants with simple integration patterns, when the plants are obtained by simple microprojectile bombardment without inducing a double stranded DNA break, and without providing the foreign DNA with homology to the genomic regions flanking the preselected site.

In a convenient embodiment of the invention, the target plant cell comprises in its genome a marker gene, flanked by two recognition sites for a rare-cleaving double stranded DNA break inducing endonuclease, one on each side. This marker DNA may be introduced in the genome of the plant cell of interest using any method of transformation, or may have been introduced into the genome of a plant cell of another plant line or variety (such a as a plant line or variety easy amenable to transformation) and introduced into the plant cell of interest by classical breeding techniques. Preferably, the population of transgenic plants or plant cells comprising a marker gene flanked by two recognition sites for a rare-cleaving double stranded break inducing endonuclease has been analysed for the expression pattern of the marker gene (such as high expression, temporally or spatially regulated expression) and the plant lines with the desired expression pattern identified. Production of a transgenic plant by microprojectile bombardment comprising the steps of
(a) inducing a double stranded DNA break at a preselected site in the genome of a cell of a plant, in accordance with the methods described elsewhere in this document or available in the art; and
(b) introducing the foreign DNA of interest into the plant cell by microprojectile bombardment wherein said foreign DNA of interest is flanked by two DNA regions having at least 80% sequence identity to the DNA regions flanking the preselected site in the genome of the plant;

will lead to transgenic plant cells and plants wherein the marker gene has been replaced by the foreign DNA of interest.

The marker gene may be any selectable or a screenable plant-expressible marker gene, which is preferably a conventional chimeric marker gene. The chimeric marker gene can comprise a marker DNA that is under the control of, and operatively linked at its 5' end to, a promoter, preferably a constitutive plant-expressible promoter, such as a CaMV 35S promoter, or a light inducible promoter such as the promoter of the gene encoding the small subunit of Rubisco; and operatively linked at its 3' end to suitable plant transcription termination and polyadenylation signals. The marker DNA preferably encodes an RNA, protein or polypeptide which, when expressed in the cells of a plant, allows such cells to be readily separated from those cells in which the marker DNA is not expressed. The choice of the marker DNA is not critical, and any suitable marker DNA can be selected in a well known manner. For example, a marker DNA can encode a protein that provides a distinguishable color to the transformed plant cell, such as the A1 gene (Meyer et al. (1987), *Nature* 330: 677), can encode a fluorescent protein [Chalfie et al, *Science* 263: 802-805 (1994); Crameri et al, *Nature Biotechnology* 14: 315-319 (1996)], can encode a protein that provides herbicide resistance to the transformed plant cell, such as the bar gene, encoding PAT which provides resistance to phosphinothricin (EP 0242246), or can encode a protein that provides antibiotic resistance to the transformed cells, such as the aac(6') gene, encoding GAT which provides resistance to gentamycin (WO 94/01560). Such selectable marker gene generally encodes a protein that confers to the cell resistance to an antibiotic or other chemical compound that is normally toxic for the cells. In plants the selectable marker gene may thus also encode a protein that confers resistance to a herbicide, such as a herbicide comprising a glutamine synthetase inhibitor (e.g. phosphinothricin) as an active ingredient. An example of such genes are genes encoding phosphinothricin acetyl transferase such as the sfr or sfrv genes (EP 242236; EP 242246; De Block et al., 1987 *EMBO J.* 6: 2513-2518).

The introduced repair DNA may further comprise a marker gene that allows to better discriminate between integration by homologous recombination at the preselected site and the integration elsewhere in the genome. Such marker genes are available in the art and include marker genes whereby the absence of the marker gene can be positively selected for under selective conditions (e.g. codA, cytosyine deaminase from *E. coli* conferring sensitivity to 5-fluoro cytosine, Perera et al. 1993 *Plant Mol. Biol.* 23, 793; Stougaard (1993) *Plant J.*: 755). The repair DNA needs to comprise the marker gene in such a way that integration of the repair DNA into the nuclear genome in a random way results in the presence of the marker gene whereas the integration of the repair DNA by homologous recombination results in the absence of the marker gene.

It will be immediately clear that the same results can also be obtained using only one preselected site at which to induce the double stranded break, which is located in or near a marker gene. The flanking regions of homology are then preferably chosen in such way as to either inactivate the marker gene, or delete the marker gene and substitute for the foreign DNA to be inserted.

It will be appreciated that the means and methods of the invention are particularly useful for corn, but may also be used in other plants with similar effects, particularly in cereal plants including wheat, oat, barley, rice, turfgrass, sorghum, millet or sugarcane plants. The methods of the invention can also be applied to any plant including but not limited to cotton, tobacco, canola, oilseed rape, soybean, vegetables, potatoes, *Lemna* spp., *Nicotiana* spp., *Arabidopsis*, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

It is also an object of the invention to provide plant cells and plants comprising foreign DNA molecules inserted at preselected sites, according to the methods of the invention. Gametes, seeds, embryos, either zygotic or somatic, progeny or hybrids of plants comprising the targeted DNA insertion events, which are produced by traditional breeding methods are also included within the scope of the present invention.

The plants obtained by the methods described herein may be further crossed by traditional breeding techniques with other plants to obtain progeny plants comprising the targeted DNA insertion events obtained according to the present invention.

The following non-limiting Examples describe the design of a modified I-SceI encoding chimeric gene, and the use thereof to insert foreign DNA into a preselected site of the plant genome.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:

SEQ ID No 1: amino acid sequence of a chimeric I-SceI comprising a nuclear localization signal linked to a I-SceI protein lacking the 4 amino-terminal amino acids.
SEQ ID No 2: nucleotide sequence of I-SceI coding region (UIPAC code).
SEQ ID No 3: nucleotide sequence of synthetic I-SceI coding region (UIPAC code).
SEQ ID No 4: nucleotide sequence of synthetic I-SceI coding region.
SEQ ID No 5: nucleotide sequence of the T-DNA of pTTAM78 (target locus).
SEQ ID No 6: nucleotide sequence of the T-DNA of pTTA82 (repair DNA).
SEQ ID No 7: nucleotide sequence of pCV78.

TABLE 1

(corresponding to SEQ ID 2)

| Tri-nucleotide | AA | Possible trinucleotides | UIPAC code | PROVISIO |
|---|---|---|---|---|
| R1 | M | ATG | ATG | |
| R2 | A | GCA GCC GCG GCT | GCN | |
| R3 | K | AAA AAG | AAR | |
| R4 | P | CCA CCC CCG CCT | CCN | |
| R5 | P | CCA CCC CCG CCT | CCN | |
| R6 | K | AAA AAG | AAR | |
| R7 | K | AAA AAG | AAR | |
| R8 | K | AAA AAG | AAR | |
| R9 | R | AGA AGG CGA CGC CGG CGT | AGR or CGN | |
| R10 | K | AAA AAG | AAR | NOT AAG |
| R11 | V | GTA GTC GTG GTT | GTN | |
| R12 | N | AAC AAT | AAY | IF R12 AAT NOT (R13 ATT OR R13 ATA). IF R12 AAC NOT (R13 ATT AND R14 AAA) IF R12 AAC NOT R13 ATA |
| R13 | I | ATA ATC ATT | ATH | IF R13 ATT NOT R14 AAA IF R13 ATA NOT R14 AAA |
| R14 | K | AAA AAG | AAR | |
| R15 | K | AAA AAG | AAR | |
| R16 | N | AAC AAT | AAY | |
| R17 | Q | CAA CAG | CAR | NOT CAA |
| R18 | V | GTA GTC GTG GTT | GTN | NOT GTA |
| R19 | M | ATG | ATG | |
| R20 | N | AAC AAT | AAY | AVOID ATTTA |
| R21 | L | TTA TTG CTA CTC CTG CTT | TTR or CTN | |
| R22 | G | GGA GGC GGG GGT | GGN | |
| R23 | P | CCA CCC CCG CCT | CCN | IF R23 CCC NOT R24 AAT |
| R24 | N | AAC AAT | AAY | |
| R25 | S | AGC AGT TCA TCC TCG TCT | AGY or TCN | |
| R26 | K | AAA AAG | AAR | IF R26 AAA NOT (R27 TTG AND R28 CTN) |
| R27 | L | TTA TTG CTA CTC CTG CTT | TTR or CTN | IF R27 (TTA OR CTA) NOT R28 TTA |
| R28 | L | TTA TTG CTA CTC CTG CTT | TTR or CTN | |
| R29 | K | AAA AAG | AAR | |
| R30 | E | GAA GAG | GAR | NOT GAA |
| R31 | Y | TAC TAT | TAY | IF R31 TAT NOT R32 AAA |

TABLE 1-continued (corresponding to SEQ ID 2)

| Tri-nucleotide | AA | Possible trinucleotides | UIPAC code | PROVISIO |
|---|---|---|---|---|
| R32 | K | AAA AAG | AAR | |
| R33 | S | AGC AGT TCA TCC TCG TCT | AGY or TCN | IF R33 (TCC OR TCG OR AGC) NOT (R34 CAA AND R35 TTR) |
| R34 | Q | CAA CAG | CAR | IF R34 CAA NOT R35 TTA |
| R35 | L | TTA TTG CTA CTC CTG CTT | TTR or CTN | |
| R36 | I | ATA ATC ATT | ATH | |
| R37 | E | GAA GAG | GAR | IF R37 GAA NOT R38 TTA |
| R38 | L | TTA TTG CTA CTC CTG CTT | TTR or CTN | |
| R39 | N | AAC AAT | AAY | IF R39 AAT NOT R40 (ATT OR ATA) |
| R40 | I | ATA ATC ATT | ATH | |
| R41 | E | GAA GAG | GAR | IF R41 GAG NOT R42 CAA |
| R42 | Q | CAA CAG | CAR | |
| R43 | F | TTC TTT | TTY | |
| R44 | E | GAA GAG | GAR | |
| R45 | A | GCA GCC GCG GCT | GCN | NOT GCA |
| R46 | G | GGA GGC GGG GGT | GGN | |
| R47 | I | ATA ATC ATT | ATH | NOT ATT |
| R48 | G | GGA GGC GGG GGT | GGN | IF R48 GGA NOT R49 TTA |
| R49 | L | TTA TTG CTA CTC CTG CTT | TTR or CTN | IF R49 TTA NOT (R50 ATA AND R51 TTR) IF R49 CTA NOT (R50 ATA AND R51 TTR) |
| R50 | I | ATA ATC ATT | ATH | IF R50 ATA NOT R51 (CTA OR TTG) |
| R51 | L | TTA TTG CTA CTC CTG CTT | TTR or CTN | |
| R52 | G | GGA GGC GGG GGT | GGN | |
| R53 | D | GAC GAT | GAY | |
| R54 | A | GCA GCC GCG GCT | GCN | IF R54 GCA NOT R55 TAC |
| R55 | Y | TAC TAT | TAY | IF R55 TAT NOT (R56 ATA AND R57 AGR) |
| R56 | I | ATA ATC ATT | ATH | |
| R57 | R | AGA AGG CGA CGC CGG CGT | AGR or CGN | |
| R58 | S | AGC AGT TCA TCC TCG TCT | AGY or TCN | AVOID GCAGG |
| R59 | R | AGA AGG CGA CGC CGG CGT | AGR or CGN | |
| R60 | D | GAC GAT | GAY | |

TABLE 1-continued (corresponding to SEQ ID 2)

| Tri-nucleotide | AA | Possible trinucleotides | UIPAC code | PROVISIO |
|---|---|---|---|---|
| R61 | E | GAA GAG | GAR | AVOID AAGGT |
| R62 | G | GGA GGC GGG GGT | GGN | |
| R63 | K | AAA AAG | AAR | |
| R64 | T | ACA ACC ACG ACT | ACN | |
| R65 | Y | TAC TAT | TAY | IF R65 TAT NOT R66 TGC |
| R66 | C | TGC TGT | TGY | |
| R67 | M | ATG | ATG | |
| R68 | Q | CAA CAG | CAR | NOT CAA |
| R69 | F | TTC TTT | TTY | |
| R70 | E | GAA GAG | GAR | |
| R71 | W | TGG | TGG | |
| R72 | K | AAA AAG | AAR | |
| R73 | N | AAC AAT | AAY | NOT AAT |
| R74 | K | AAA AAG | AAR | IF R74 AAA NOT R75 GCA |
| R75 | A | GCA GCC GCG GCT | GCN | IF R75 GCA NOT R76 TAC |
| R76 | Y | TAC TAT | TAY | |
| R77 | M | ATG | ATG | |
| R78 | D | GAC GAT | GAY | |
| R79 | H | CAC CAT | CAY | |
| R80 | V | GTA GTC GTG GTT | GTN | |
| R81 | C | TGC TGT | TGY | |
| R82 | L | TTA TTG CTA CTC CTG CTT | TTR or CTN | |
| R83 | L | TTA TTG CTA CTC CTG CTT | TTR or CTN | |
| R84 | Y | TAC TAT | TAY | |
| R85 | D | GAC GAT | GAY | IF R85 GAC NOT R86 CAA |
| R86 | Q | CAA CAG | CAR | |
| R87 | W | TGG | TGG | |
| R88 | V | GTA GTC GTG GTT | GTN | |
| R89 | L | TTA TTG CTA CTC CTG CTT | TTR or CTN | |
| R90 | S | AGC AGT TCA TCC TCG TCT | AGY or TCN | |
| R91 | P | CCA CCC CCG CCT | CCN | |
| R92 | P | CCA CCC CCG CCT | CCN | |
| R93 | H | CAC CAT | CAY | IF R93 CAT NOT R94 AAA |

TABLE 1-continued (corresponding to SEQ ID 2)

| Tri-nucleotide | AA | Possible trinucleotides | UIPAC code | PROVISIO |
|---|---|---|---|---|
| R94 | K | AAA AAG | AAR | |
| R95 | K | AAA AAG | AAR | |
| R96 | E | GAA GAG | GAR | |
| R97 | R | AGA AGG CGA CGC CGG CGT | AGR or CGN | |
| R98 | V | GTA GTC GTG GTT | GTN | |
| R99 | N | AAC AAT | AAY | |
| R100 | H | CAC CAT | CAY | AVOID ATTTA |
| R101 | L | TTA TTG CTA CTC CTG CTT | TTR or CTN | |
| R102 | G | GGA GGC GGG GGT | GGN | IF R102 GGC NOT R103 AAT |
| R103 | N | AAC AAT | AAY | AVOID ATTTA |
| R104 | L | TTA TTG CTA CTC CTG CTT | TTR or CTN | |
| R105 | V | GTA GTC GTG GTT | GTN | |
| R106 | I | ATA ATC ATT | ATH | |
| R107 | T | ACA ACC ACG ACT | ACN | |
| R108 | W | TGG | TGG | |
| R109 | G | GGA GGC GGG GGT | GGN | |
| R110 | A | GCA GCC GCG GCT | GCN | |
| R111 | Q | CAA CAG | CAR | |
| R112 | T | ACA ACC ACG ACT | ACN | AVOID ATTTA |
| R113 | F | TTC TTT | TTY | |
| R114 | K | AAA AAG | AAR | IF R114 AAG NOT R115 CAT |
| R115 | H | CAC CAT | CAY | |
| R116 | Q | CAA CAG | CAR | IF R116 CAA NOT R117 GCA |
| R117 | A | GCA GCC GCG GCT | GCN | AVOID ATTTA |
| R118 | F | TTC TTT | TTY | |
| R119 | N | AAC AAT | AAY | NOT AAT |
| R120 | K | AAA AAG | AAR | IF R120 AAA NOT R121 TTG |
| R121 | L | TTA TTG CTA CTC CTG CTT | TTR or CTN | |
| R122 | A | GCA GCC GCG GCT | GCN | IF R122 GCC NOT R123 AAT |
| R123 | N | AAC AAT | AAY | AVOID ATTTA |
| R124 | L | TTA TTG CTA CTC CTG CTT | TTR or CTN | |
| R125 | F | TTC TTT | TTY | |

TABLE 1-continued (corresponding to SEQ ID 2)

| Trinucleotide | AA | Possible trinucleotides | UIPAC code | PROVISIO |
|---|---|---|---|---|
| R126 | I | ATA ATC ATT | ATH | |
| R127 | V | GTA GTC GTG GTT | GTN | |
| R128 | N | AAC AAT | AAY | IF R128 AAT NOT R129 AAT |
| R129 | N | AAC AAT | AAY | NOT AAT |
| R130 | K | AAA AAG | AAR | |
| R131 | K | AAA AAG | AAR | |
| R132 | T | ACA ACC ACG ACT | ACN | |
| R133 | I | ATA ATC ATT | ATH | |
| R134 | P | CCA CCC CCG CCT | CCN | IF R134 CCC NOT R135 AAT |
| R135 | N | AAC AAT | AAY | IF R135 AAT NOT R136 AAT |
| R136 | N | AAC AAT | AAY | AVOID ATTTA |
| R137 | L | TTA TTG CTA CTC CTG CTT | TTR or CTN | |
| R138 | V | GTA GTC GTG GTT | GTN | |
| R139 | E | GAA GAG | GAR | |
| R140 | N | AAC AAT | AAY | |
| R141 | Y | TAC TAT | TAY | AVOID ATTTA |
| R142 | L | TTA TTG CTA CTC CTG CTT | TTR or CTN | |
| R143 | T | ACA ACC ACG ACT | ACN | |
| R144 | P | CCA CCC CCG CCT | CCN | NOT CCA |
| R145 | M | ATG | ATG | |
| R146 | S | AGC AGT TCA TCC TCG TCT | AGY or TCN | IF R146 TCA NOT R147 TTG |
| R147 | L | TTA TTG CTA CTC CTG CTT | TTR or CTN | |
| R148 | A | GCA GCC GCG GCT | GCN | |
| R149 | Y | TAC TAT | TAY | NOT TAT |
| R150 | W | TGG | TGG | |
| R151 | F | TTC TTT | TTY | |
| R152 | M | ATG | ATG | |
| R153 | D | GAC GAT | GAY | |
| R154 | D | GAC GAT | GAY | |
| R155 | G | GGA GGC GGG GGT | GGN | |
| R156 | G | GGA GGC GGG GGT | GGN | |
| R157 | K | AAA AAG | AAR | |
| R158 | W | TGG | TGG | |

TABLE 1-continued (corresponding to SEQ ID 2)

| Tri-nucleo-tide | AA | Possible trinucleotides | UIPAC code | PROVISIO |
|---|---|---|---|---|
| R159 | D | GAC GAT | GAY | |
| R160 | Y | TAC TAT | TAY | |
| R161 | N | AAC AAT | AAY | NOT AAT |
| R162 | K | AAA AAG | AAR | IF R162 AAA NOT (R163 AAT AND R164 AGY) |
| R163 | N | AAC AAT | AAY | |
| R164 | S | AGC AGT TCA TCC TCG TCT | AGY or TCN | IF R164 TCA NOT (R165 ACC AND R166 AAY) |
| R165 | T | ACA ACC ACG ACT | ACN | IF R165 ACC NOT R166 AAT |
| R166 | N | AAC AAT | AAY | NOT AAT |
| R167 | K | AAA AAG | AAR | IF R167 AAA R168 NOT TCA OR R168 NOT AGC |
| R168 | S | AGC AGT TCA TCC TCG TCT | AGY or TCN | |
| R169 | I | ATA ATC ATT | ATH | |
| R170 | V | GTA GTC GTG GTT | GTN | IF R170 GTA NOT R171TTA |
| R171 | L | TTA TTG CTA CTC CTG CTT | TTR or CTN | |
| R172 | N | AAC AAT | AAY | IF R172 AAT NOT R173 ACA |
| R173 | T | ACA ACC ACG ACT | ACN | IF R173 (ACC OR ACG) NOT (R174 CAA AND R175 TCN) |
| R174 | Q | CAA CAG | CAR | |
| R175 | S | AGC AGT TCA TCC TCG TCT | AGY or TCN | AVOID ATTTA |
| R176 | F | TTC TTT | TTY | |
| R177 | T | ACA ACC ACG ACT | ACN | |
| R178 | F | TTC TTT | TTY | |
| R179 | E | GAA GAG | GAR | |
| R180 | E | GAA GAG | GAR | |
| R181 | V | GTA GTC GTG GTT | GTN | |
| R182 | E | GAA GAG | GAR | IF R182 GAA NOT (R183 TAT AND R184 TTR) |
| R183 | Y | TAC TAT | TAY | AVOID ATTTA |
| R184 | L | TTA TTG CTA CTC CTG CTT | TTR or CTN | |
| R185 | V | GTA GTC GTG GTT | GTN | |
| R186 | K | AAA AAG | AAR | |
| R187 | G | GGA GGC GGG GGT | GGN | IF R187 GGA NOT (R188 TTG AND R189 CGN) |
| R188 | L | TTA TTG CTA CTC CTG CTT | TTR or CTN | |

TABLE 1-continued (corresponding to SEQ ID 2)

| Tri-nucleo-tide | AA | Possible trinucleotides | UIPAC code | PROVISIO |
|---|---|---|---|---|
| R189 | R | AGA AGG CGA CGC CGG CGT | AGR or CGN | IF R189 CGC NOT R190 AAT |
| R190 | N | AAC AAT | AAY | NOT AAT |
| R191 | K | AAA AAG | AAR | |
| R192 | F | TTC TTT | TTY | IF R192 TTC NOT (R193 CAA AND R194 TTR) |
| R193 | Q | CAA CAG | CAR | IF R193 CAA NOT R194 TTA |
| R194 | L | TTA TTG CTA CTC CTG CTT | TTR or CTN | |
| R195 | N | AAC AAT | AAY | IF R195 AAT NOT R196 TGC |
| R196 | C | TGC TGT | TGY | |
| R197 | Y | TAC TAT | TAY | |
| R198 | V | GTA GTC GTG GTT | GTN | |
| R199 | K | AAA AAG | AAR | NOT AAA |
| R200 | I | ATA ATC ATT | ATH | IF R200 ATT NOT R201 AAT NOT ATA |
| R201 | N | AAC AAT | AAY | NOT AAT |
| R202 | K | AAA AAG | AAR | IF R202 AAA NOT R203 AAT |
| R203 | N | AAC AAT | AAY | NOT AAT |
| R204 | K | AAA AAG | AAR | |
| R205 | P | CCA CCC CCG CCT | CCN | NOT CCA IF R205 CCG NOT R206 ATA |
| R206 | I | ATA ATC ATT | ATH | IF R206 ATA NOT R207 ATA |
| R207 | I | ATA ATC ATT | ATH | IF R207 ATA NOT R208 TAC NOT ATT |
| R208 | Y | TAC TAT | TAY | |
| R209 | I | ATA ATC ATT | ATH | |
| R210 | D | GAC GAT | GAY | |
| R211 | S | AGC AGT TCA TCC TCG TCT | AGY or TCN | |
| R212 | M | ATG | ATG | |
| R213 | S | AGC AGT TCA TCC TCG TCT | AGY or TCN | |
| R214 | Y | TAC TAT | TAY | AVOID ATTA |
| R215 | L | TTA TTG CTA CTC CTG CTT | TTR or CTN | IF R215 (TTA OR CTA) NOT R216 ATA |
| R216 | I | ATA ATC ATT | ATH | |
| R217 | F | TTC TTT | TTY | |
| R218 | Y | TAC TAT | TAY | |
| R219 | N | AAC AAT | AAY | AVOID ATTA |

TABLE 1-continued (corresponding to SEQ ID 2)

| Tri-nucleo-tide | AA | Possible trinucleotides | UIPAC code | PROVISIO |
|---|---|---|---|---|
| R220 | L | TTA TTG CTA CTC CTG CTT | TTR or CTN | IF R220 (TTA OR CTA) NOT R221 ATT<br>IF R220 (TTA OR CTA) NOT R221 ATC |
| R221 | I | ATA ATC ATT | ATH | IF R221 ATT NOT R222 AAA<br>NOT ATA |
| R222 | K | AAA AAG | AAR | |
| R223 | P | CCA CCC CCG CCT | CCN | |
| R224 | Y | TAC TAT | TAY | AVOID ATTTA |
| R225 | L | TTA TTG CTA CTC CTG CTT | TTR or CTN | |
| R226 | I | ATA ATC ATT | ATH | |
| R227 | P | CCA CCC CCG CCT | CCN | |
| R228 | Q | CAA CAG | CAR | |
| R229 | M | ATG | ATG | |
| R230 | M | ATG | ATG | |
| R231 | Y | TAC TAT | TAY | IF R231TAT NOT R232 AAA |
| R232 | K | AAA AAG | AAR | IF R232 AAA NOT R233 TTG |
| R233 | L | TTA TTG CTA CTC CTG CTT | TTR or CTN | |
| R234 | P | CCA CCC CCG CCT | CCN | IF 234 CCC NOT R235 AAT |
| R235 | N | AAC AAT | AAY | IF R235 AAT NOT R236 ACA<br>IF R235 AAT NOT R236 ACT |
| R236 | T | ACA ACC ACG ACT | ACN | IF R236 ACA NOT (R237 ATA AND R238 AGY) |
| R237 | I | ATA ATC ATT | ATH | |
| R238 | S | AGC AGT TCA TCC TCG TCT | AGY or TCN | |
| R239 | S | AGC AGT TCA TCC TCG TCT | AGY or TCN | |
| R240 | E | GAA GAG | GAR | |
| R241 | T | ACA ACC ACG ACT | ACN | |
| R242 | F | TTC TTT | TTY | |
| R243 | L | TTA TTG CTA CTC CTG CTT | TTR or CTN | |
| R244 | K | AAA AAG | AAR | |

TABLE 2
(corresponding to SEQ ID No 3)

| Tri-nucleotide | AA | Choices | UIPAC | PROVISIO | Exemplified I-SceI (SEQ ID No 4) |
|---|---|---|---|---|---|
| R1 | M | ATG | ATG | | ATG |
| R2 | A | GCC GCT | GCY | | GCC |
| R3 | K | AAA AAG | AAR | | AAG |
| R4 | P | CCA CCC CCT | CCH | | CCT |
| R5 | P | CCA CCC CCT | CCH | | CCC |
| R6 | K | AAA AAG | AAR | | AAG |
| R7 | K | AAA AAG | AAR | | AAG |
| R8 | K | AAA AAG | AAR | | AAG |
| R9 | R | AGA CGC CGG | AGA or CGS | | CGC |
| R10 | K | AAA | AAA | | AAA |
| R11 | V | GTC GTG | GTS | | GTG |
| R12 | N | AAC | AAC | | AAC |
| R13 | I | ATC ATT | ATY | | ATC |
| R14 | K | AAA AAG | AAR | | AAG |
| R15 | K | AAA AAG | AAR | | AAG |
| R16 | N | AAC | AAC | | AAC |
| R17 | Q | CAG | CAG | | CAG |
| R18 | V | GTC GTG | GTS | | GTG |
| R19 | M | ATG | ATG | | ATG |
| R20 | N | AAC | AAC | | AAC |
| R21 | L | CTC CTG | CTS | | CTG |
| R22 | G | GGC GGA | GGM | | GGA |
| R23 | P | CCA CCC CCT | CCH | | CCT |
| R24 | N | AAC | AAC | | AAC |
| R25 | S | AGC TCA TCC | AGC or TCM | | AGC |
| R26 | K | AAA AAG | AAR | | AAG |
| R27 | L | CTC CTG | CTS | | CTC |
| R28 | L | CTC CTG | CTS | | CTG |
| R29 | K | AAA AAG | AAR | | AAG |
| R30 | E | GAG | GAG | | GAG |
| R31 | Y | TAC | TAC | | TAC |
| R32 | K | AAA AAG | AAR | | AAG |
| R33 | S | AGC TCA TCC | AGC or TCM | | AGC |
| R34 | Q | CAA CAG | CAR | | CAG |
| R35 | L | CTC CTG | CTS | | CTG |
| R36 | I | ATC ATT | ATY | | ATC |
| R37 | E | GAA GAG | GAR | | GAA |
| R38 | L | CTC CTG | CTS | | CTG |
| R39 | N | AAC | AAC | | AAC |
| R40 | I | ATC ATT | ATY | | ATC |
| R41 | E | GAA GAG | GAR | IF R41 GAG NOT R42 CAA | GAG |
| R42 | Q | CAA CAG | CAR | | CAG |
| R43 | F | TTC | TTC | | TTC |
| R44 | E | GAA GAG | GAR | | GAA |
| R45 | A | GCC GCT | GCY | | GCT |
| R46 | G | GGC GGA | GGM | | GGC |
| R47 | I | ATC | ATC | | ATC |
| R48 | G | GGC GGA | GGM | | GGC |
| R49 | L | CTC CTG | CTS | | CTG |
| R50 | I | ATC ATT | ATY | | ATC |
| R51 | L | CTC CTG | CTS | | CTG |
| R52 | G | GGC GGA | GGM | | GGC |
| R53 | D | GAC GAT | GAY | | GAT |
| R54 | A | GCC GCT | GCY | | GCC |
| R55 | Y | TAC | TAC | | TAC |
| R56 | I | ATC ATT | ATY | | ATC |
| R57 | R | AGA CGC CGG | AGA or CGS | | AGA |
| R58 | S | AGC TCA TCC | AGC or TCM | | TCC |
| R59 | R | AGA CGC CGG | AGA or CGS | | CGG |
| R60 | D | GAC GAT | GAY | | GAC |
| R61 | E | GAA GAG | GAR | | GAA |
| R62 | G | GGC GGA | GGM | | GGC |
| R63 | K | AAA AAG | AAR | | AAG |
| R64 | T | ACC ACT | ACY | | ACC |
| R65 | Y | TAC | TAC | | TAC |
| R66 | C | TGC TGT | TGY | | TGC |

TABLE 2-continued

(corresponding to SEQ ID No 3)

| Tri-nucleo-tide | AA Choices | UIPAC | PROVISIO | Exemplified I-ScI (SEQ ID No 4) |
|---|---|---|---|---|
| R67 | M ATG | ATG | | ATG |
| R68 | Q CAG | CAG | | CAG |
| R69 | F TTC | TTC | | TTC |
| R70 | E GAA GAG | GAR | | GAG |
| R71 | W TGG | TGG | | TGG |
| R72 | K AAA AAG | AAR | | AAG |
| R73 | N AAC | AAC | | AAC |
| R74 | K AAA AAG | AAR | | AAG |
| R75 | A GCC GCT | GCY | | GCC |
| R76 | Y TAC | TAC | | TAC |
| R77 | M ATG | ATG | | ATG |
| R78 | D GAC GAT | GAY | | GAC |
| R79 | H CAC CAT | CAY | | CAC |
| R80 | V GTC GTG | GTS | | GTG |
| R81 | C TGC TGT | TGY | | TGT |
| R82 | L CTC CTG | CTS | | CTG |
| R83 | L CTC CTG | CTS | | CTG |
| R84 | Y TAC | TAC | | TAC |
| R85 | D GAC GAT | GAY | IF R85 GAC NOT R86 CAA | GAC |
| R86 | Q CAA CAG | CAR | | CAG |
| R87 | W TGG | TGG | | TGG |
| R88 | V GTC GTG | GTS | | GTC |
| R89 | L CTC CTG | CTS | | CTG |
| R90 | S AGC TCA TCC | AGC or TCM | | AGC |
| R91 | P CCA CCC CCT | CCH | | CCT |
| R92 | P CCA CCC CCT | CCH | | CCT |
| R93 | H CAC CAT | CAY | IF R93 CAT NOT R94 AAA | CAC |
| R94 | K AAA AAG | AAR | | AAG |
| R95 | K AAA AAG | AAR | | AAG |
| R96 | E GAA GAG | GAR | | GAG |
| R97 | R AGA CGC CGG | AGA or CGS | | CGC |
| R98 | V GTC GTG | GTS | | GTG |
| R99 | N AAC | AAC | | AAC |
| R100 | H CAC CAT | CAY | | CAT |
| R101 | L CTC CTG | CTS | | CTG |
| R102 | G GGC GGA | GGM | | GGC |
| R103 | N AAC | AAC | | AAC |
| R104 | L CTC CTG | CTS | | CTC |
| R105 | V GTC GTG | GTS | | GTG |
| R106 | I ATC ATT | ATY | | ATC |
| R107 | T ACC ACT | ACY | | ACC |
| R108 | W TGG | TGG | | TGG |
| R109 | G GGC GGA | GGM | | GGA |
| R110 | A GCC GCT | GCY | | GCC |
| R111 | Q CAA CAG | CAR | | CAG |
| R112 | T ACC ACT | ACY | | ACC |
| R113 | F TTC | TTC | | TTC |
| R114 | K AAA AAG | AAR | IF R114 AAG NOT R115 CAT | AAG |
| R115 | H CAC CAT | CAY | | CAC |
| R116 | Q CAA CAG | CAR | | CAG |
| R117 | A GCC GCT | GCY | | GCC |
| R118 | F TTC | TTC | | TTC |
| R119 | N AAC | AAC | | AAC |
| R120 | K AAA AAG | AAR | | AAG |
| R121 | L CTC CTG | CTS | | CTG |
| R122 | A GCC GCT | GCS | | GCC |
| R123 | N AAC | AAC | | AAC |
| R124 | L CTC CTG | CTS | | CTG |
| R125 | F TTC | TTC | | TTC |
| R126 | I ATC ATT | ATY | | ATC |
| R127 | V GTC GTG | CTS | | GTG |
| R128 | N AAC | AAC | | AAC |
| R129 | N AAC | AAC | | AAC |
| R130 | K AAA AAG | AAR | | AAG |
| R131 | K AAA AAG | AAR | | AAG |
| R132 | T ACC ACT | ACY | | ACC |
| R133 | I ATC ATT | ATY | | ATC |
| R134 | P CCA CCC CCT | CCH | | CCC |

TABLE 2-continued (corresponding to SEQ ID No 3)

| Tri-nucleo-tide | AA | Choices | UIPAC | PROVISIO | Exemplified I-SceI (SEQ ID No 4) |
|---|---|---|---|---|---|
| R135 | N | AAC | AAC | | AAC |
| R136 | N | AAC | AAC | | AAC |
| R137 | L | CTC CTG | CTS | | CTC |
| R138 | V | GTC GTG | GTS | | GTG |
| R139 | E | GAA GAG | GAR | | GAG |
| R140 | N | AAC | AAC | | AAC |
| R141 | Y | TAC | TAC | | TAC |
| R142 | L | CTC CTG | CTS | | CTC |
| R143 | T | ACC ACT | ACY | | ACT |
| R144 | P | CCC CCT | CCY | | CCC |
| R145 | M | ATG | ATG | | ATG |
| R146 | S | AGC TCA TCC | AGC or TCM | | AGC |
| R147 | L | CTC CTG | CTS | | CTG |
| R148 | A | GCC GCT | GCY | | GCC |
| R149 | Y | TAC | TAC | | TAC |
| R150 | W | TGG | TGG | | TGG |
| R151 | F | TTC | TTC | | TTC |
| R152 | M | ATG | ATG | | ATG |
| R153 | D | GAC GAT | GAY | | GAC |
| R154 | D | GAC GAT | GAY | | GAC |
| R155 | G | GGC GGA | GGM | | GGA |
| R156 | G | GGC GGA | GGM | | GGC |
| R157 | K | AAA AAG | AAR | | AAG |
| R158 | W | TGG | TGG | | TGG |
| R159 | D | GAC GAT | GAY | | GAC |
| R160 | Y | TAC | TAC | | TAC |
| R161 | N | AAC | AAC | | AAC |
| R162 | K | AAA AAG | AAR | | AAG |
| R163 | N | AAC | AAC | | AAC |
| R164 | S | AGC TCA TCC | AGC or TCM | IF R164 TCA NOT R165 ACC | AGC |
| R165 | T | ACC ACT | ACY | | ACC |
| R166 | N | AAC | AAC | | AAC |
| R167 | K | AAA AAG | AAR | IF R167 AAA R168 NOT TCA OR R168 NOT AGC | AAG |
| R168 | S | AGC TCA TCC | AGC or TCM | | TCA |
| R169 | I | ATC ATT | ATY | | ATT |
| R170 | V | GTC GTG | GTS | | GTG |
| R171 | L | CTC CTG | CTS | | CTG |
| R172 | N | AAC | AAC | | AAC |
| R173 | T | ACC ACT | ACY | IF R173 ACC NOT (R174 CAA AND R175 TCN) | ACC |
| R174 | Q | CAA CAG | CAR | | CAA |
| R175 | S | AGC TCA TCC | AGC or TCM | | AGC |
| R176 | F | TTC | TTC | | TTC |
| R177 | T | ACC ACT | ACY | | ACC |
| R178 | F | TTC | TTC | | TTC |
| R179 | E | GAA GAG | GAR | | GAA |
| R180 | E | GAA GAG | GAR | | GAA |
| R181 | V | GTC GTG | GTS | | GTG |
| R182 | E | GAA GAG | GAR | | GAG |
| R183 | Y | TAC | TAC | | TAC |
| R184 | L | CTC CTG | CTS | | CTC |
| R185 | V | GTC GTG | GTS | | GTC |
| R186 | K | AAA AAG | AAR | | AAG |
| R187 | G | GGC GGA | GGM | | GGC |
| R188 | L | CTC CTG | CTS | | CTG |
| R189 | R | AGA CGC CGG | AGA or CGS | | CGC |
| R190 | N | AAC | AAC | | AAC |
| R191 | K | AAA AAG | AAR | | AAG |
| R192 | F | TTC | TTC | | TTC |
| R193 | Q | CAA CAG | CAR | | CAG |
| R194 | L | CTC CTG | CTS | | CTG |
| R195 | N | AAC | AAC | | AAC |
| R196 | C | TGC TGT | TGY | | TGC |
| R197 | Y | TAC | TAC | | TAC |
| R198 | V | GTC GTG | GTS | | GTG |
| R199 | K | AAG | AAG | | AAG |

TABLE 2-continued (corresponding to SEQ ID No 3)

| Tri-nucleo-tide | AA | Choices | UIPAC | PROVISIO | Exemplified I-SceI (SEQ ID No 4) |
|---|---|---|---|---|---|
| R200 | I | ATC ATT | ATY | | ATC |
| R201 | N | AAC | AAC | | AAC |
| R202 | K | AAA AAG | AAR | | AAG |
| R203 | N | AAC | AAC | | AAC |
| R204 | K | AAA AAG | AAR | | AAG |
| R205 | P | CCC CCT | CCY | | CCT |
| R206 | I | ATC ATT | ATY | | ATC |
| R207 | I | ATC | ATC | | ATC |
| R208 | Y | TAC | TAC | | TAC |
| R209 | I | ATC ATT | ATY | | ATC |
| R210 | D | GAC GAT | GAY | | GAC |
| R211 | S | AGC TCA TCC | AGC or TCM | | AGC |
| R212 | M | ATG | ATG | | ATG |
| R213 | S | AGC TCA TCC | AGC or TCM | | AGC |
| R214 | Y | TAC | TAC | | TAC |
| R215 | L | CTC CTG | CTS | | CTG |
| R216 | I | ATC ATT | ATY | | ATC |
| R217 | F | TTC | TTC | | TTC |
| R218 | Y | TAC | TAC | | TAC |
| R219 | N | AAC | AAC | | AAC |
| R220 | L | CTC CTG | CTS | | CTG |
| R221 | I | ATC ATT | ATY | IF R221 ATT NOT R222 AAA | ATC |
| R222 | K | AAA AAG | AAR | | AAG |
| R223 | P | CCA CCC CCT | CCH | | CCA |
| R224 | Y | TAC | TAC | | TAC |
| R225 | L | CTC CTG | CTS | | CTG |
| R226 | I | ATC ATT | ATY | | ATC |
| R227 | P | CCA CCC CCT | CCH | | CCT |
| R228 | Q | CAA CAG | CAR | | CAG |
| R229 | M | ATG | ATG | | ATG |
| R230 | M | ATG | ATG | | ATG |
| R231 | Y | TAC | TAC | | TAC |
| R232 | K | AAA AAG | AAR | | AAG |
| R233 | L | CTC CTG | CTS | | CTG |
| R234 | P | CCA CCC CCT | CCH | | CCC |
| R235 | N | AAC | AAC | | AAC |
| R236 | T | ACC ACT | ACY | | ACC |
| R237 | I | ATC ATT | ATY | | ATC |
| R238 | S | AGC TCA TCC | AGC or TCM | | AGC |
| R239 | S | AGC TCA TCC | AGC or TCM | | AGC |
| R240 | E | GAA GAG | GAR | | GAG |
| R241 | T | ACC ACT | ACY | | ACC |
| R242 | F | TTC | TTC | | TTC |
| R243 | L | CTC CTG | CTS | | CTG |
| R244 | K | AAA AAG | AAR | | AAG |

EXAMPLES

Example I

Design, Synthesis and Analysis of a Plant Expressible Chimeric Gene Encoding I-SceI The coding region of I-SceI wherein the 4 aminoterminal amino acids have been replaced by a nuclear localization signal was optimized using the following process:
1. Change the codons to the most preferred codon usage for maize without altering the amino acid sequence of I-SceI protein, using the Synergy Geneoptimizer™;
2. Adjust the sequence to create or eliminate specific restriction sites to exchange the synthetic I-SceI coding region with the universal code I-SceI gene;
3. Eliminate all GC stretches longer than 6 bp and AT stretches longer than 4 bp to avoid formation of secondary RNA structures than can effect pre-mRNA splicing
4. Avoid CG and TA duplets in codon positions 2 and 3;
5. Avoid other regulatory elements such as possible premature polyadenylation signals (GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA), cryptic intron splice sites (AAGGTAAGT and TGCAGG), ATTTA pentamers and CCAAT box sequences (CCAAT, ATTGG, CGAAT and ATTGC);
6. Recheck if the adapted coding region fulfill all of the above mentioned criteria.

A possible example of such a nucleotide sequence is represented in SEQ ID No 4. A synthetic DNA fragment having the nucleotide sequence of SEQ ID No 4 was synthesized and operably linked to a CaMV35S promoter and a CaMV35S 3' termination and polyadenylation signal (yielding plasmid pCV78; SEQ ID No 7).

The synthetic I-SceI coding region was also cloned into a bacterial expression vector (as a fusion protein allowing protein enrichment on amylose beads). The capacity of semi-purified I-SceI protein to cleave in vitro a plasmid containing an I-SceI recognition site was verified.

Example 2

Isolation of Maize Cell Lines Containing a Promoterless Bar Gene Preceded by an I-SceI Site In order to develop an assay for double stranded DNA break induced homology-mediated recombination, maize cell suspensions were isolated that contained a promoterless bar gene preceded by an I-SceI recognition site integrated in the nuclear genome in single copy. Upon double stranded DNA break induction through delivery of an I-SceI endonuclease encoding plant expressible chimeric gene, and co-delivery of repair DNA comprising a CaMV 35S promoter operably linked to the 5' end of the bar gene, the 35S promoter may be inserted through homology mediated targeted DNA insertion, resulting in a functional bar gene allowing resistance to phosphinotricin (PPT). The assay is schematically represented in FIG. 1.

The target locus was constructed by operably linking through conventional cloning techniques the following DNA regions
a) a 3' end termination and polyadenylation signal from the nopaline synthetase gene
b) a promoter-less bar encoding DNA region
c) a DNA region comprising an I-SceI recognition site
d) a 3' end termination and polyadenylation signal from *A. tumefaciens* gene 7 (3'g7)
e) a plant expressible neomycin resistance gene comprising a nopaline synthetase promoter, a neomycine phosphotransferase gene, and a 3' ocs signal.
This DNA region was inserted in a T-DNA vector between the T-DNA borders. The T-DNA vector was designated pTTAM78 (for nucleotide sequence of the T-DNA see SEQ ID No 5)

The T-DNA vector was used directly to transform protoplasts of corn according to the methods described in EP 0 469 273, using a He89-derived corn cell suspension. The T-DNA vector was also introduced into *Agrobacterium tumefaciens* C58C1Rif(pEHA101) and the resulting *Agrobacterium* was used to transform an He89-derived cell line. A number of target lines were identified that contained a single copy of the target locus construct pTTAM78, such as T24 (obtained by protoplast transformation) and lines 14-1 and 1-20 (obtained by *Agrobacterium* mediated transformation).

Cell suspensions were established from these target lines in N6M cell suspension medium, and grown in the light on a shaker (120 rpm) at 25° C. Suspensions were subcultured every week.

Example 3

Homology Based Targeted Insertion

The repair DNA pTTA82 is a T-DNA vector containing between the T-DNA borders the following operably linked DNA regions:

a) a DNA region encoding only the aminoterminal part of the bar gene
b) a DNA region comprising a partial I-SceI recognition site (13 nucleotides located at the 5' end of the recognition site)
c) a CaMV 35S promoter region
d) a DNA region comprising a partial I-SceI recognition site (9 nucleotides located at the 3' end of the recognition site)
e) a 3' end termination and polyadenylation signal from *A. tumefaciens* gene 7 (3'g7)
f) a chimeric plant expressible neomycine resistance gene
g) a defective I-SceI endonuclease encoding gene under control of a CaMV 35S promoter
The nucleotide sequence of the T-DNA of pTTA82 is represented in SEQ ID NO 6.

This repair DNA was co-delivered with pCV78 (see Example 1) by particle bombardment into suspension derived cells which were plated on filter paper as a thin layer. The filter paper was plated on Mahq1 VII substrate.

The DNA was bombarded into the cells using a PDS-1000/He Biolistics device. Microcarrier preparation and coating of DNA onto microcarriers was essentially as described by Sanford et al. 1992. Particle bombardment parameters were: target distance of 9 cm; bombardment pressure of 1350 psi, gap distance of ¼" and macrocarrier flight distance of 11 cm. Immediately after bombardment the tissue was transferred onto non-selective Mhi1VII substrate. As a control for successful delivery of DNA by particle bombardment, the three target lines were also bombarded with microcarriers coated with plasmid DNA comprising a chimeric bar gene under the control of a CaMV35S promoter (pRVA52).

Four days after bombardment, the filters were transferred onto Mh1 VII substrate supplemented with 25 mg/L PPT or on Ahx1.5VIIino1000 substrate supplemented with 50 mg/L PPT.

Fourteen days later, the filters were transferred onto fresh Mh1 VII medium with 10 mg/L PPT for the target lines T24 and 14-1 and Mh1 VII substrate with 25 mg/L PPT for target line 1-20.

Two weeks later, potential targeted insertion events were scored based on their resistance to PPT. These PPT resistant events were also positive in the Liberty Link Corn Leaf/Seed test (Strategic Diagnostics Inc.).

Number of PPT Resistant Calli 38 Days After Bombardment:

|  | pRVA52 | | pTTA82 + pCV78 | |
| --- | --- | --- | --- | --- |
| Target line | Total number of PPT$^R$ events | Mean number of PPT$^R$ events/petridish | Total number of PPT$^R$ events | Mean number of PPT$^R$ events/petridish |
| 1-20 | 75 | 25 | 115 | 7.6 |
| 14-1 | 37 | 12.3 | 38 | 2.2 |
| 24 | 40 | 13.3 | 2 | 0.13 |

The PPT resistant events were further subcultured on Mh1 VII substrate containing 10 mg/L PPT and callus material was used for molecular analysis. Twenty independent candidate TSI were analyzed by Southern analysis using the 35S promoter and the 3' end termination and polyadenylation signal from the nopaline synthase gene as a probe. Based on the size of the expected fragment, all events appeared to be perfect targeted sequence insertion events. Moreover, further analysis of about half of the targeted sequence insertion events did not show additional non-targeted integration of either the repair DNA or the I-SceI encoding DNA.

Sequence analysis of DNA amplified from eight of the targeted insertion events demonstrated that these events were indeed perfect homologous recombination based TSI events.

Based on these data, the ratio of homologous recombination based DNA insertion versus the "normal" illegitimate recombination varies from about 30% for 1-20 to about 17% for 14-1 and to about 1% for 24.

When using vectors similar to the ones described in Puchta et al, 1996 (supra) delivered by electroporation to tobacco protoplasts in the presence of I-SceI induced double stranded DNA breaks, the ratio of homologous recombination based DNA insertion versus normal insertion was about 15%. However, only one of out of 33 characterized events was a homology-mediated targeted sequence insertion event whereby the homologous recombination was perfect at both sides of the double stranded break.

Using the vectors from Example 2, but with a "universal code I-SceI construct" comprising a nuclear localization signal, the ratio of HR based DNA insertion versus normal insertion varied between 0.032% and 16% for different target lines, both using electroporation or Agrobacterium mediated DNA delivery. The relative frequency of perfect targeted insertion events differed between the different target lines, and varied from 8 to 70% for electroporation mediated DNA delivery and between 73 to 90% for Agrobacterium mediated DNA delivery.

Example 4

Acetosyringone Pre-Incubation Improves the Frequency of Recovery of Targeted Insertion Events One week before bombardment as described in Example 3, cell suspensions were either diluted in N6M medium or in LSIDhy1.5 medium supplemented with 200 μM acetosyringone. Otherwise, the method as described in Example 3 was employed. As can be seen from the results summarized in the following table, preincubation of the cells to be transformed with acetosyringone had a beneficial effect on the recovery of targeted PPT resistant insertion events.

|  | Preincubation with acetosyringone | | No preincubation | |
|---|---|---|---|---|
| Target line | Total number of $PPT^R$ events | Mean number of $PPT^R$ events/petridish | Total number of $PPT^R$ events | Mean number of $PPT^R$ events/petridish |
| 1-20 | 89 | 7.6 | 26 | 3.7 |
| 14-1 | 32 | 3.6 | 6 | 0.75 |
| 24 | 0 | 0 | 2 | 0.3 |

Example 5

DSB-mediated targeted sequence insertion in maize by Agrobacterium-Mediated Delivery of Repair DNA To analyze DSB-mediated targeted sequence insertion in maize, whereby the repair DNA is delivered by Agrobacterium-mediated transformation, T-DNA vectors were constructed similar to pTTA82 (see Example 3), wherein the defective I-SceI was replaced by the synthetic I-SceI encoding gene of Example 1. The T-DNA vector further contained a copy of the Agrobacterium tumefaciens virg and virc (pTCV83) or virg, virc and virB (pTCV87) outside the T-DNA borders. These T-DNA vectors were inserted into LBA4404, containing the helper Ti-plasmid pAL4404, yielding Agrobacterium strains A4995 and A 4996 respectively.

Suspension cultures of the target cell lines of Example 2, as well as other target cell lines obtained in a similar way as described in Example 2, were co-cultivated with the Agrobacterium strains, and plated thereafter on a number of plates. The number of platings was determined by the density of the cell suspension. As a control for the transformation efficiency, the cell suspension were co-cultivated in a parallel experiment with an Agrobacterium strain LBA4404 containing helper Ti-plasmid pAL4404 and a T-DNA vector with a chimeric phosphinotricin resistance gene (bar gene) under control of a CaMV 35S vector. The T-DNA vector further contained a copy of the Agrobacterium tumefaciens virG, virC and virB genes, outside the T-DNA border. The results of four different independent experiments are summarized in the tables below:

Agrobacterium Experiment I:

|  | Control | | A4495 | |
|---|---|---|---|---|
| Target line | N° of platings | N° of transformants | N° of platings[1] | N° of TSI events |
| T24 | 26 | 10 | 32 | 0 |
| T26 | 36 | 44 | 36 | 1 |
| 14-1 | 20 | 18 | 28 | 0 |
| T1 F155 | 26 | 7 | 24 | 0 |

Agrobacterium Experiment II:

|  | Control | | A4495 | |
|---|---|---|---|---|
| Target line | N° of platings | N° of transformants | N° of platings[1] | N° of TSI events |
| 1-20 | 18 | ~200 | 27 | 11 |
| T79 | 24 | ~480 | 24 | 6 |
| T66 | 26 | 73 | 31 | 0 |
| T5 | 28 | 35 | 18 | 0 |
| T1 F154 | 22 | 65 | 16 | 1 |

Agrobacterium Experiment III:

|  | Control | | A4496 | |
|---|---|---|---|---|
| Target line | N° of platings | N° of transformants | N° of platings[1] | N° of TSI events |
| T24 | 50 | ~2250 | 30 | 1 |
| T26 | 44 | ~220 | 32 | 1 |
| 14-1 | 20 | ~1020 | 13 | 1 |
| T1 F155 | 33 | ~1870 | 32 | 0 |

Agrobacterium Experiment IV:

|  | A3970 | | A4496 | |
|---|---|---|---|---|
| Target line | N° of platings | N° of transformants | N° of platings[1] | N° of TSI events |
| T1 F154 |  |  | 28 | 1 |
| T5 | 12 | ~600 | 28 | 1 |

| | A3970 | | A4496 | |
|---|---|---|---|---|
| Target line | N° of platings | N° of transformants | N° of platings[(1)] | N° of TSI events |
| T66 | | | 28 | 0 |
| T79 | | | 24 | 0 |
| 1-20 | 18 | ~400 | 40 | 9 |

Thus, it is clear that, while *Agrobacterium*-mediated repair DNA delivery is clearly feasible, the frequency of Targeted Sequence Insertion (TSI) events is lower in comparison with particle bombardment-mediated repair DNA delivery. Southern analysis performed on 23 putative TSI events showed that 20 TSI events are perfect, based on the size of the fragment. However, in contrast with the events obtained by microprojectile bombardment as in Example 3, only 6 events out of 20 did not contain additional inserts of the repair DNA, 9 events did contain 1 to 3 additional inserts of the repair DNA, and 5 events contained many additional inserts of the repair DNA.

Particle bombardment mediated delivery of repair DNA also results in better quality of DSB mediated TSI events compared to delivery of repair DNA by *Agrobacterium*. This is in contrast for particle bombardment mediated delivery of "normal transforming DNA" which is characterized by the lesser quality of the transformants (complex integration pattern) in comparison with *Agrobacterium*-mediated transformation.

This indicates that the quality of transformants obtained by particle bombardment or other direct DNA delivery methods can be improved by DSB mediated insertion of sequences. This result is also confirmed by the following experiment: upon DSB mediated targeted sequence insertion of a 35S promoter, in absence of flanking sequences with homology to the target locus in the repair DNA, we observed that upon electroporation-mediated delivery of repair DNA, only a minority of the TSI events did contain additional non-targeted insertions of 35S promoter (2 TSI events out of 16 analyzed TSI events show additional at random insertion(s) of the 35S promoter). In contrast random insertion of the 35S promoter was considerably higher in TSI events obtained by *Agrobacterium* mediated delivery of the 35S promoter (17 out 22 analyzed TSI events showed additional at random insertion(s) of the 35S promoter).

Example 6

Media Composition

Mahq1VII: N6 medium (Chu et al. 1975) supplemented with 100 mg/L casein hydrolysate, 6 mM L-proline, 0.5 g/L 2-(N-morpholino)ethanesulfonic acid (MES), 0.2M mannitol, 0.2M sorbitol, 2% sucrose, 1 mg/L 2,4-dichlorophenoxy acetic acid (2,4-D), adjusted to pH5.8, solidified with 2.5 g/L Gelrite®.

Mhi1VII: N6 medium (Chu et al. 1975) supplemented with 0.5 g/L 2-(N-morpholino)ethanesulfonic acid (MES), 0.2M mannitol, 2% sucrose, 1 mg/L 2,4-dichlorophenoxy acetic acid (2,4-D), adjusted to pH5.8 solidified with 2.5 g/L Gelrite®.

Mh1VII: idem to Mhi1VII substrate but without 0.2 M mannitol.

Ahx1.5VIIino1000: MS salts, supplemented with 1000 mg/L myo-inositol, 0.1 mg/L thiamine-HCl, 0.5 mg/L nicotinic acid, 0.5 mg/L pyridoxine-HCl, 0.5 g/L MES, 30 g/L sucrose, 10 g/L glucose, 1.5 mg/L 2,4-D, adjusted to pH 5.8 solidified with 2.5 g/L Gelrite®.

LSIDhy1.5: MS salts supplemented with 0.5 mg/L nicotinic acid, 0.5 mg/L pyridoxine-HCl, 1 mg/L thiamine-HCl, 100 mg/L myo-inositol, 6 mM L-proline, 0.5 g/L MES, 20 g/L sucrose, 10 g/L glucose, 1.5 mg/L 2.4-D, adjusted to pH 5.2.

N6M: macro elements: 2830 mg/L $KNO_3$; 433 mg/L $(NH_4)_2SO_4$; 166 mg/L $CaCl_2.2H_2O$; 250 mg/L $MgSO_4.7H_2O$; 400 mg/L $KH_2PO_4$; 37.3 mg/L $Na_2EDTA$; 27.3 mg/L $FeSO_4.7H_2O$, MS micro elements, 500 mg/L Bactotrypton, 0.5 g/L MES, 1 mg/L thiamin-HCl, 0.5 mg/L nicotinic acid, 0.5 mg/L pyridoxin-HCl, 2 mg/L glycin, 100 mg/L myo-inositol, 3% sucrose, 0.5 mg/L 2.4-D, adjusted to pH5.8.

What is claimed is:

1. A method for introducing a foreign DNA of interest into a preselected site of a genome of a plant cell comprising the steps of
   (a) inducing a double stranded DNA break at a recognition site for a double stranded DNA break inducing (DSBI) enzyme at said preselected site in the genome of the cell, wherein said double stranded break is introduced by a DSBI enzyme recognizing said recognition site; and
   (b) introducing the foreign DNA of interest into the plant cell by direct DNA transfer, wherein said foreign DNA of interest is introduced into said plant cell in the absence of flanking sequences (i) with at least 80% sequence identity to a DNA region immediately flanking the preselected site and (ii) that are at least 10 nucleotides in length.

2. The method of claim 1, wherein said direct DNA transfer is accomplished by bombardment of microprojectiles coated with the foreign DNA of interest.

3. The method of claim 1, wherein said double stranded DNA break inducing enzyme is a I-SceI endonuclease.

4. The method of claim 1, wherein the plant cell is a maize cell.

5. The method of claim 4, wherein the maize cell is comprised within a cell suspension.

6. The method of claim 1, wherein said plant cell is incubated in a plant phenolic compound prior to step a).

7. The method of claim 6, wherein said plant phenolic compound is acetosyringone (3,5-dimethoxy-4-hydroxyacetophenone), α-hydroxy-acetosyringone, sinapinic acid (3,5 dimethoxy-4-hydroxycinnamic acid), syringic acid (4-hydroxy-3,5 dimethoxybenzoic acid), ferulic acid (4-hydroxy-3-methoxycinnamic acid), catechol (1,2-dihydroxybenzene), p-hydroxybenzoic acid (4-hydroxybenzoic acid), β-resorcylic acid (2,4 dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) or vanillin (3-methoxy-4-hydroxybenzaldehyde).

8. The method of claim 1, wherein said double stranded DNA break inducing enzyme comprises a nuclear localization signal.

9. The method of claim 1, wherein said direct DNA transfer is accomplished by introduction of DNA by electroporation.

10. The method of claim 1, wherein said direct DNA transfer is accomplished by introduction of DNA by electroporation into intact plant cells or partially degraded tissues or plant cells.

11. The method of claim 7, wherein said plant phenolic compound is acetosyringone.

12. The method of claim 1, wherein said DSBI enzyme is a rare-cleaving endonuclease.

13. The method of claim 1, wherein said DSBI enzyme is a custom designed rare-cleaving endonuclease.

* * * * *

SEQUENCE LISTING

```
<160> NUMBER OF SEQ ID NOS: 7

<210> SEQ ID NO 1
<211> LENGTH: 244
<212> TYPE: PRT
<213> ORGANISM: Saccharomyces cerevisiae

<400> SEQUENCE: 1

Met Ala Lys Pro Pro Lys Lys Arg Lys Val Asn Ile Lys Lys Asn
1               5                   10                  15

Gln Val Met Asn Leu Gly Pro Asn Ser Lys Leu Leu Lys Glu Tyr Lys
            20                  25                  30

Ser Gln Leu Ile Glu Leu Asn Ile Glu Gln Phe Glu Ala Gly Ile Gly
        35                  40                  45

Leu Ile Leu Gly Asp Ala Tyr Ile Arg Ser Arg Asp Glu Gly Lys Thr
    50                  55                  60

Tyr Cys Met Gln Phe Glu Trp Lys Asn Lys Ala Tyr Met Asp His Val
65                  70                  75                  80

Cys Leu Leu Tyr Asp Gln Trp Val Leu Ser Pro Pro His Lys Lys Glu
```

-continued

```
                        85                  90                  95
Arg Val Asn His Leu Gly Asn Leu Val Ile Thr Trp Gly Ala Gln Thr
            100                 105                 110

Phe Lys His Gln Ala Phe Asn Lys Leu Ala Asn Leu Phe Ile Val Asn
            115                 120                 125

Asn Lys Lys Thr Ile Pro Asn Leu Val Glu Asn Tyr Leu Thr Pro
            130                 135                 140

Met Ser Leu Ala Tyr Trp Phe Met Asp Asp Gly Gly Lys Trp Asp Tyr
145                 150                 155                 160

Asn Lys Asn Ser Thr Asn Lys Ser Ile Val Leu Asn Thr Gln Ser Phe
                165                 170                 175

Thr Phe Glu Glu Val Glu Tyr Leu Val Lys Gly Leu Arg Asn Lys Phe
            180                 185                 190

Gln Leu Asn Cys Tyr Val Lys Ile Asn Lys Asn Lys Pro Ile Ile Tyr
            195                 200                 205

Ile Asp Ser Met Ser Tyr Leu Ile Phe Tyr Asn Leu Ile Lys Pro Tyr
            210                 215                 220

Leu Ile Pro Gln Met Met Tyr Lys Leu Pro Asn Thr Ile Ser Ser Glu
225                 230                 235                 240

Thr Phe Leu Lys

<210> SEQ ID NO 2
<211> LENGTH: 732
<212> TYPE: DNA
<213> ORGANISM: Artificial
<220> FEATURE:
<223> OTHER INFORMATION: synthetic DNA sequence encoding I-SceI
      (UIPAC code)
<220> FEATURE:
<221> NAME/KEY: misc_feature
<222> LOCATION: (6)..(6)
<223> OTHER INFORMATION: N=A,G,C or T
<220> FEATURE:
<221> NAME/KEY: variation
<222> LOCATION: (25)..(27)
<223> OTHER INFORMATION: AGR
<220> FEATURE:
<221> NAME/KEY: variation
<222> LOCATION: (61)..(63)
<223> OTHER INFORMATION: TTR
<220> FEATURE:
<221> NAME/KEY: variation
<222> LOCATION: (73)..(75)
<223> OTHER INFORMATION: AGY
<220> FEATURE:
<221> NAME/KEY: variation
<222> LOCATION: (79)..(81)
<223> OTHER INFORMATION: TTR
<220> FEATURE:
<221> NAME/KEY: variation
<222> LOCATION: (82)..(84)
<223> OTHER INFORMATION: TTR
<220> FEATURE:
<221> NAME/KEY: variation
<222> LOCATION: (97)..(99)
<223> OTHER INFORMATION: AGY
<220> FEATURE:
<221> NAME/KEY: variation
<222> LOCATION: (103)..(105)
<223> OTHER INFORMATION: TTR
<220> FEATURE:
<221> NAME/KEY: variation
<222> LOCATION: (112)..(114)
<223> OTHER INFORMATION: TTR
<220> FEATURE:
<221> NAME/KEY: variation
<222> LOCATION: (145)..(147)
<223> OTHER INFORMATION: TTR
<220> FEATURE:
```

```
<221> NAME/KEY: variation
<222> LOCATION: (151)..(153)
<223> OTHER INFORMATION: TTR
<220> FEATURE:
<221> NAME/KEY: variation
<222> LOCATION: (169)..(171)
<223> OTHER INFORMATION: AGR
<220> FEATURE:
<221> NAME/KEY: variation
<222> LOCATION: (172)..(174)
<223> OTHER INFORMATION: AGY
<220> FEATURE:
<221> NAME/KEY: variation
<222> LOCATION: (175)..(177)
<223> OTHER INFORMATION: AGR
<220> FEATURE:
<221> NAME/KEY: variation
<222> LOCATION: (244)..(246)
<223> OTHER INFORMATION: TTR
<220> FEATURE:
<221> NAME/KEY: variation
<222> LOCATION: (247)..(249)
<223> OTHER INFORMATION: TTR
<220> FEATURE:
<221> NAME/KEY: variation
<222> LOCATION: (265)..(267)
<223> OTHER INFORMATION: TTR
<220> FEATURE:
<221> NAME/KEY: variation
<222> LOCATION: (268)..(270)
<223> OTHER INFORMATION: AGY
<220> FEATURE:
<221> NAME/KEY: variation
<222> LOCATION: (289)..(291)
<223> OTHER INFORMATION: AGR
<220> FEATURE:
<221> NAME/KEY: variation
<222> LOCATION: (301)..(303)
<223> OTHER INFORMATION: TTR
<220> FEATURE:
<221> NAME/KEY: variation
<222> LOCATION: (310)..(312)
<223> OTHER INFORMATION: TTR
<220> FEATURE:
<221> NAME/KEY: variation
<222> LOCATION: (361)..(363)
<223> OTHER INFORMATION: TTR
<220> FEATURE:
<221> NAME/KEY: variation
<222> LOCATION: (370)..(372)
<223> OTHER INFORMATION: TTR
<220> FEATURE:
<221> NAME/KEY: variation
<222> LOCATION: (409)..(411)
<223> OTHER INFORMATION: TTR
<220> FEATURE:
<221> NAME/KEY: variation
<222> LOCATION: (424)..(426)
<223> OTHER INFORMATION: TTR
<220> FEATURE:
<221> NAME/KEY: variation
<222> LOCATION: (436)..(438)
<223> OTHER INFORMATION: AGY
<220> FEATURE:
<221> NAME/KEY: variation
<222> LOCATION: (439)..(441)
<223> OTHER INFORMATION: TTR
<220> FEATURE:
<221> NAME/KEY: variation
<222> LOCATION: (490)..(492)
<223> OTHER INFORMATION: AGY
<220> FEATURE:
<221> NAME/KEY: variation
<222> LOCATION: (502)..(504)
<223> OTHER INFORMATION: AGY
<220> FEATURE:
<221> NAME/KEY: variation
<222> LOCATION: (511)..(513)
<223> OTHER INFORMATION: TTR
<220> FEATURE:
```

```
<221> NAME/KEY: variation
<222> LOCATION: (523)..(525)
<223> OTHER INFORMATION: AGY
<220> FEATURE:
<221> NAME/KEY: variation
<222> LOCATION: (550)..(552)
<223> OTHER INFORMATION: TTR
<220> FEATURE:
<221> NAME/KEY: variation
<222> LOCATION: (562)..(564)
<223> OTHER INFORMATION: TTR
<220> FEATURE:
<221> NAME/KEY: variation
<222> LOCATION: (565)..(567)
<223> OTHER INFORMATION: AGR
<220> FEATURE:
<221> NAME/KEY: variation
<222> LOCATION: (580)..(582)
<223> OTHER INFORMATION: TTR
<220> FEATURE:
<221> NAME/KEY: variation
<222> LOCATION: (631)..(633)
<223> OTHER INFORMATION: AGY
<220> FEATURE:
<221> NAME/KEY: variation
<222> LOCATION: (637)..(639)
<223> OTHER INFORMATION: AGY
<220> FEATURE:
<221> NAME/KEY: variation
<222> LOCATION: (643)..(645)
<223> OTHER INFORMATION: TTR
<220> FEATURE:
<221> NAME/KEY: variation
<222> LOCATION: (658)..(660)
<223> OTHER INFORMATION: TTR
<220> FEATURE:
<221> NAME/KEY: variation
<222> LOCATION: (673)..(675)
<223> OTHER INFORMATION: TTR
<220> FEATURE:
<221> NAME/KEY: variation
<222> LOCATION: (697)..(699)
<223> OTHER INFORMATION: TTR
<220> FEATURE:
<221> NAME/KEY: variation
<222> LOCATION: (712)..(714)
<223> OTHER INFORMATION: AGY
<220> FEATURE:
<221> NAME/KEY: variation
<222> LOCATION: (715)..(717)
<223> OTHER INFORMATION: AGY
<220> FEATURE:
<221> NAME/KEY: variation
<222> LOCATION: (727)..(729)
<223> OTHER INFORMATION: TTR
<220> FEATURE:
<221> NAME/KEY: misc_feature
<222> LOCATION: (12)..(12)
<223> OTHER INFORMATION: N = A, G, C or T
<220> FEATURE:
<221> NAME/KEY: misc_feature
<222> LOCATION: (15)..(15)
<223> OTHER INFORMATION: N = A, G, C or T
<220> FEATURE:
<221> NAME/KEY: misc_feature
<222> LOCATION: (27)..(27)
<223> OTHER INFORMATION: N = A, G, C or T
<220> FEATURE:
<221> NAME/KEY: misc_feature
<222> LOCATION: (33)..(33)
<223> OTHER INFORMATION: N = A, G, C or T
<220> FEATURE:
<221> NAME/KEY: misc_feature
<222> LOCATION: (54)..(54)
<223> OTHER INFORMATION: N = A, G, C or T
<220> FEATURE:
<221> NAME/KEY: misc_feature
<222> LOCATION: (63)..(63)
<223> OTHER INFORMATION: N = A, G, C or T
<220> FEATURE:
```

```
<221> NAME/KEY: misc_feature
<222> LOCATION: (66)..(66)
<223> OTHER INFORMATION: N = A, G, C or T
<220> FEATURE:
<221> NAME/KEY: misc_feature
<222> LOCATION: (69)..(69)
<223> OTHER INFORMATION: N = A, G, C or T
<220> FEATURE:
<221> NAME/KEY: misc_feature
<222> LOCATION: (75)..(75)
<223> OTHER INFORMATION: N = A, G, C or T
<220> FEATURE:
<221> NAME/KEY: misc_feature
<222> LOCATION: (81)..(81)
<223> OTHER INFORMATION: N = A, G, C or T
<220> FEATURE:
<221> NAME/KEY: misc_feature
<222> LOCATION: (84)..(84)
<223> OTHER INFORMATION: N = A, G, C or T
<220> FEATURE:
<221> NAME/KEY: misc_feature
<222> LOCATION: (99)..(99)
<223> OTHER INFORMATION: N = A, G, C or T
<220> FEATURE:
<221> NAME/KEY: misc_feature
<222> LOCATION: (105)..(105)
<223> OTHER INFORMATION: N = A, G, C or T
<220> FEATURE:
<221> NAME/KEY: misc_feature
<222> LOCATION: (114)..(114)
<223> OTHER INFORMATION: N = A, G, C or T
<220> FEATURE:
<221> NAME/KEY: misc_feature
<222> LOCATION: (135)..(135)
<223> OTHER INFORMATION: N = A, G, C or T
<220> FEATURE:
<221> NAME/KEY: misc_feature
<222> LOCATION: (138)..(138)
<223> OTHER INFORMATION: N = A, G, C or T
<220> FEATURE:
<221> NAME/KEY: misc_feature
<222> LOCATION: (144)..(144)
<223> OTHER INFORMATION: N = A, G, C or T
<220> FEATURE:
<221> NAME/KEY: misc_feature
<222> LOCATION: (147)..(147)
<223> OTHER INFORMATION: N = A, G, C or T
<220> FEATURE:
<221> NAME/KEY: misc_feature
<222> LOCATION: (153)..(153)
<223> OTHER INFORMATION: N = A, G, C or T
<220> FEATURE:
<221> NAME/KEY: misc_feature
<222> LOCATION: (156)..(156)
<223> OTHER INFORMATION: N = A, G, C or T
<220> FEATURE:
<221> NAME/KEY: misc_feature
<222> LOCATION: (162)..(162)
<223> OTHER INFORMATION: N = A, G, C or T
<220> FEATURE:
<221> NAME/KEY: misc_feature
<222> LOCATION: (171)..(171)
<223> OTHER INFORMATION: N = A, G, C or T
<220> FEATURE:
<221> NAME/KEY: misc_feature
<222> LOCATION: (174)..(174)
<223> OTHER INFORMATION: N = A, G, C or T
<220> FEATURE:
<221> NAME/KEY: misc_feature
<222> LOCATION: (177)..(177)
<223> OTHER INFORMATION: N = A, G, C or T
<220> FEATURE:
<221> NAME/KEY: misc_feature
<222> LOCATION: (186)..(186)
<223> OTHER INFORMATION: N = A, G, C or T
<220> FEATURE:
<221> NAME/KEY: misc_feature
<222> LOCATION: (192)..(192)
<223> OTHER INFORMATION: N = A, G, C or T
<220> FEATURE:
```

-continued

```
<221> NAME/KEY: misc_feature
<222> LOCATION: (225)..(225)
<223> OTHER INFORMATION: N = A, G, C or T
<220> FEATURE:
<221> NAME/KEY: misc_feature
<222> LOCATION: (240)..(240)
<223> OTHER INFORMATION: N = A, G, C or T
<220> FEATURE:
<221> NAME/KEY: misc_feature
<222> LOCATION: (246)..(246)
<223> OTHER INFORMATION: N = A, G, C or T
<220> FEATURE:
<221> NAME/KEY: misc_feature
<222> LOCATION: (249)..(249)
<223> OTHER INFORMATION: N = A, G, C or T
<220> FEATURE:
<221> NAME/KEY: misc_feature
<222> LOCATION: (264)..(264)
<223> OTHER INFORMATION: N = A, G, C or T
<220> FEATURE:
<221> NAME/KEY: misc_feature
<222> LOCATION: (267)..(267)
<223> OTHER INFORMATION: N = A, G, C or T
<220> FEATURE:
<221> NAME/KEY: misc_feature
<222> LOCATION: (270)..(270)
<223> OTHER INFORMATION: N = A, G, C or T
<220> FEATURE:
<221> NAME/KEY: misc_feature
<222> LOCATION: (273)..(273)
<223> OTHER INFORMATION: N = A, G, C or T
<220> FEATURE:
<221> NAME/KEY: misc_feature
<222> LOCATION: (276)..(276)
<223> OTHER INFORMATION: N = A, G, C or T
<220> FEATURE:
<221> NAME/KEY: misc_feature
<222> LOCATION: (291)..(291)
<223> OTHER INFORMATION: N = A, G, C or T
<220> FEATURE:
<221> NAME/KEY: misc_feature
<222> LOCATION: (294)..(294)
<223> OTHER INFORMATION: N = A, G, C or T
<220> FEATURE:
<221> NAME/KEY: misc_feature
<222> LOCATION: (303)..(303)
<223> OTHER INFORMATION: N = A, G, C or T
<220> FEATURE:
<221> NAME/KEY: misc_feature
<222> LOCATION: (306)..(306)
<223> OTHER INFORMATION: N = A, G, C or T
<220> FEATURE:
<221> NAME/KEY: misc_feature
<222> LOCATION: (312)..(312)
<223> OTHER INFORMATION: N = A, G, C or T
<220> FEATURE:
<221> NAME/KEY: misc_feature
<222> LOCATION: (315)..(315)
<223> OTHER INFORMATION: N = A, G, C or T
<220> FEATURE:
<221> NAME/KEY: misc_feature
<222> LOCATION: (321)..(321)
<223> OTHER INFORMATION: N = A, G, C or T
<220> FEATURE:
<221> NAME/KEY: misc_feature
<222> LOCATION: (327)..(327)
<223> OTHER INFORMATION: N = A, G, C or T
<220> FEATURE:
<221> NAME/KEY: misc_feature
<222> LOCATION: (330)..(330)
<223> OTHER INFORMATION: N = A, G, C or T
<220> FEATURE:
<221> NAME/KEY: misc_feature
<222> LOCATION: (336)..(336)
<223> OTHER INFORMATION: N = A, G, C or T
<220> FEATURE:
<221> NAME/KEY: misc_feature
<222> LOCATION: (351)..(351)
<223> OTHER INFORMATION: N = A, G, C or T
<220> FEATURE:
```

```
<221> NAME/KEY: misc_feature
<222> LOCATION: (363)..(363)
<223> OTHER INFORMATION: N = A, G, C or T
<220> FEATURE:
<221> NAME/KEY: misc_feature
<222> LOCATION: (366)..(366)
<223> OTHER INFORMATION: N = A, G, C or T
<220> FEATURE:
<221> NAME/KEY: misc_feature
<222> LOCATION: (372)..(372)
<223> OTHER INFORMATION: N = A, G, C or T
<220> FEATURE:
<221> NAME/KEY: misc_feature
<222> LOCATION: (381)..(381)
<223> OTHER INFORMATION: N = A, G, C or T
<220> FEATURE:
<221> NAME/KEY: misc_feature
<222> LOCATION: (396)..(396)
<223> OTHER INFORMATION: N = A, G, C or T
<220> FEATURE:
<221> NAME/KEY: misc_feature
<222> LOCATION: (402)..(402)
<223> OTHER INFORMATION: N = A, G, C or T
<220> FEATURE:
<221> NAME/KEY: misc_feature
<222> LOCATION: (411)..(411)
<223> OTHER INFORMATION: N = A, G, C or T
<220> FEATURE:
<221> NAME/KEY: misc_feature
<222> LOCATION: (414)..(414)
<223> OTHER INFORMATION: N = A, G, C or T
<220> FEATURE:
<221> NAME/KEY: misc_feature
<222> LOCATION: (426)..(426)
<223> OTHER INFORMATION: N = A, G, C or T
<220> FEATURE:
<221> NAME/KEY: misc_feature
<222> LOCATION: (429)..(429)
<223> OTHER INFORMATION: N = A, G, C or T
<220> FEATURE:
<221> NAME/KEY: misc_feature
<222> LOCATION: (432)..(432)
<223> OTHER INFORMATION: N = A, G, C or T
<220> FEATURE:
<221> NAME/KEY: misc_feature
<222> LOCATION: (438)..(438)
<223> OTHER INFORMATION: N = A, G, C or T
<220> FEATURE:
<221> NAME/KEY: misc_feature
<222> LOCATION: (441)..(441)
<223> OTHER INFORMATION: N = A, G, C or T
<220> FEATURE:
<221> NAME/KEY: misc_feature
<222> LOCATION: (444)..(444)
<223> OTHER INFORMATION: N = A, G, C or T
<220> FEATURE:
<221> NAME/KEY: misc_feature
<222> LOCATION: (465)..(465)
<223> OTHER INFORMATION: N = A, G, C or T
<220> FEATURE:
<221> NAME/KEY: misc_feature
<222> LOCATION: (468)..(468)
<223> OTHER INFORMATION: N = A, G, C or T
<220> FEATURE:
<221> NAME/KEY: misc_feature
<222> LOCATION: (492)..(492)
<223> OTHER INFORMATION: N = A, G, C or T
<220> FEATURE:
<221> NAME/KEY: misc_feature
<222> LOCATION: (495)..(495)
<223> OTHER INFORMATION: N = A, G, C or T
<220> FEATURE:
<221> NAME/KEY: misc_feature
<222> LOCATION: (504)..(504)
<223> OTHER INFORMATION: N = A, G, C or T
<220> FEATURE:
<221> NAME/KEY: misc_feature
<222> LOCATION: (510)..(510)
<223> OTHER INFORMATION: N = A, G, C or T
<220> FEATURE:
```

```
<221> NAME/KEY: misc_feature
<222> LOCATION: (513)..(513)
<223> OTHER INFORMATION: N = A, G, C or T
<220> FEATURE:
<221> NAME/KEY: misc_feature
<222> LOCATION: (519)..(519)
<223> OTHER INFORMATION: N = A, G, C or T
<220> FEATURE:
<221> NAME/KEY: misc_feature
<222> LOCATION: (525)..(525)
<223> OTHER INFORMATION: N = A, G, C or T
<220> FEATURE:
<221> NAME/KEY: misc_feature
<222> LOCATION: (531)..(531)
<223> OTHER INFORMATION: N = A, G, C or T
<220> FEATURE:
<221> NAME/KEY: misc_feature
<222> LOCATION: (543)..(543)
<223> OTHER INFORMATION: N = A, G, C or T
<220> FEATURE:
<221> NAME/KEY: misc_feature
<222> LOCATION: (552)..(552)
<223> OTHER INFORMATION: N = A, G, C or T
<220> FEATURE:
<221> NAME/KEY: misc_feature
<222> LOCATION: (552)..(552)
<223> OTHER INFORMATION: N = A, G, C or T
<220> FEATURE:
<221> NAME/KEY: misc_feature
<222> LOCATION: (555)..(555)
<223> OTHER INFORMATION: N = A, G, C or T
<220> FEATURE:
<221> NAME/KEY: misc_feature
<222> LOCATION: (561)..(561)
<223> OTHER INFORMATION: N = A, G, C or T
<220> FEATURE:
<221> NAME/KEY: misc_feature
<222> LOCATION: (564)..(564)
<223> OTHER INFORMATION: N = A, G, C or T
<220> FEATURE:
<221> NAME/KEY: misc_feature
<222> LOCATION: (567)..(567)
<223> OTHER INFORMATION: N = A, G, C or T
<220> FEATURE:
<221> NAME/KEY: misc_feature
<222> LOCATION: (582)..(582)
<223> OTHER INFORMATION: N = A, G, C or T
<220> FEATURE:
<221> NAME/KEY: misc_feature
<222> LOCATION: (594)..(594)
<223> OTHER INFORMATION: N = A, G, C or T
<220> FEATURE:
<221> NAME/KEY: misc_feature
<222> LOCATION: (615)..(615)
<223> OTHER INFORMATION: N = A, G, C or T
<220> FEATURE:
<221> NAME/KEY: misc_feature
<222> LOCATION: (633)..(633)
<223> OTHER INFORMATION: N = A, G, C or T
<220> FEATURE:
<221> NAME/KEY: misc_feature
<222> LOCATION: (639)..(639)
<223> OTHER INFORMATION: N = A, G, C or T
<220> FEATURE:
<221> NAME/KEY: misc_feature
<222> LOCATION: (645)..(645)
<223> OTHER INFORMATION: N = A, G, C or T
<220> FEATURE:
<221> NAME/KEY: misc_feature
<222> LOCATION: (660)..(660)
<223> OTHER INFORMATION: N = A, G, C or T
<220> FEATURE:
<221> NAME/KEY: misc_feature
<222> LOCATION: (669)..(669)
<223> OTHER INFORMATION: N = A, G, C or T
<220> FEATURE:
<221> NAME/KEY: misc_feature
<222> LOCATION: (675)..(675)
<223> OTHER INFORMATION: N = A, G, C or T
<220> FEATURE:
```

-continued

<221> NAME/KEY: misc_feature
<222> LOCATION: (681)..(681)
<223> OTHER INFORMATION: N = A, G, C or T
<220> FEATURE:
<221> NAME/KEY: misc_feature
<222> LOCATION: (699)..(699)
<223> OTHER INFORMATION: N = A, G, C or T
<220> FEATURE:
<221> NAME/KEY: misc_feature
<222> LOCATION: (702)..(702)
<223> OTHER INFORMATION: N = A, G, C or T
<220> FEATURE:
<221> NAME/KEY: misc_feature
<222> LOCATION: (708)..(708)
<223> OTHER INFORMATION: N = A, G, C or T
<220> FEATURE:
<221> NAME/KEY: misc_feature
<222> LOCATION: (714)..(714)
<223> OTHER INFORMATION: N = A, G, C or T
<220> FEATURE:
<221> NAME/KEY: misc_feature
<222> LOCATION: (717)..(717)
<223> OTHER INFORMATION: N = A, G, C or T
<220> FEATURE:
<221> NAME/KEY: misc_feature
<222> LOCATION: (723)..(723)
<223> OTHER INFORMATION: N = A, G, C or T
<220> FEATURE:
<221> NAME/KEY: misc_feature
<222> LOCATION: (729)..(729)
<223> OTHER INFORMATION: N = A, G, C or T

<400> SEQUENCE: 2
atggcnaarc cnccnaaraa raarcgnaar gtnaayatha araaraayca rgtnatgaay 60
ctnggnccna aytcnaarct nctnaargar tayaartcnc arctnathga rctnaayath 120
garcarttyg argcnggnat hggnctnath ctnggngayg cntayathcg ntcncgngay 180
garggnaara cntaytgyat gcarttygar tggaaraaya argcntayat ggaycaygtn 240
tgyctnctnt aygaycartg ggtnctntcn ccnccncaya araargarcg ngtnaaycay 300
ctnggnaayc tngtnathac ntggggngcn caracnttya arcaycargc nttyaayaar 360
ctngcnaayc tnttyathgt naayaayaar aaracnathc cnaayaayct ngtngaraay 420
tayctnacnc cnatgtcnct ngcntaytgg ttyatggayg ayggnggnaa rtgggaytay 480
aayaaraayt cnacnaayaa rtcnathgtn ctnaayacnc artcnttyac nttygargar 540
gtngartayc tngtnaargg nctncgnaay aarttycarc tnaaytgyta ygtnaarath 600
aayaaraaya arccnathat htayathgay tcnatgtcnt ayctnathtt ytayaayctn 660
athaarccnt ayctnathcc ncaratgatg tayaarctnc cnaayacnat htcntcngar 720
acnttyctna ar 732

<210> SEQ ID NO 3
<211> LENGTH: 732
<212> TYPE: DNA
<213> ORGANISM: Artificial
<220> FEATURE:
<223> OTHER INFORMATION: preferred synthetic DNA sequence encoding
I-SceI (UIPAC code)
<220> FEATURE:
<221> NAME/KEY: variation
<222> LOCATION: (25)..(27)
<223> OTHER INFORMATION: AGA
<220> FEATURE:
<221> NAME/KEY: variation
<222> LOCATION: (73)..(75)
<223> OTHER INFORMATION: AGC
<220> FEATURE:
<221> NAME/KEY: variation
<222> LOCATION: (97)..(99)
<223> OTHER INFORMATION: AGC

```
<220> FEATURE:
<221> NAME/KEY: variation
<222> LOCATION: (169)..(171)
<223> OTHER INFORMATION: AGA
<220> FEATURE:
<221> NAME/KEY: variation
<222> LOCATION: (172)..(174)
<223> OTHER INFORMATION: AGC
<220> FEATURE:
<221> NAME/KEY: variation
<222> LOCATION: (175)..(177)
<223> OTHER INFORMATION: AGA
<220> FEATURE:
<221> NAME/KEY: variation
<222> LOCATION: (268)..(270)
<223> OTHER INFORMATION: AGC
<220> FEATURE:
<221> NAME/KEY: variation
<222> LOCATION: (289)..(291)
<223> OTHER INFORMATION: AGA
<220> FEATURE:
<221> NAME/KEY: variation
<222> LOCATION: (436)..(438)
<223> OTHER INFORMATION: AGC
<220> FEATURE:
<221> NAME/KEY: variation
<222> LOCATION: (490)..(492)
<223> OTHER INFORMATION: AGC
<220> FEATURE:
<221> NAME/KEY: variation
<222> LOCATION: (502)..(504)
<223> OTHER INFORMATION: AGC
<220> FEATURE:
<221> NAME/KEY: variation
<222> LOCATION: (523)..(525)
<223> OTHER INFORMATION: AGC
<220> FEATURE:
<221> NAME/KEY: variation
<222> LOCATION: (565)..(567)
<223> OTHER INFORMATION: AGA
<220> FEATURE:
<221> NAME/KEY: variation
<222> LOCATION: (631)..(633)
<223> OTHER INFORMATION: AGC
<220> FEATURE:
<221> NAME/KEY: variation
<222> LOCATION: (637)..(639)
<223> OTHER INFORMATION: AGC
<220> FEATURE:
<221> NAME/KEY: variation
<222> LOCATION: (712)..(714)
<223> OTHER INFORMATION: AGC
<220> FEATURE:
<221> NAME/KEY: variation
<222> LOCATION: (715)..(717)
<223> OTHER INFORMATION: AGC

<400> SEQUENCE: 3
atggcyaarc chcchaaraa raarcgsaaa gtsaacatya araaraacca ggtsatgaac      60
ctsggmccha actcmaarct sctsaargag tacaartcmc arctsatyga rctsaacaty     120
garcarttcg argcyggmat cggmctsaty ctsggmgayg cytacatycg stcmcgsgay     180
garggmaara cytactgyat gcagttcgar tggaaraaca argcytacat ggaycaygts     240
tgyctsctst acgaycartg ggtsctstcm cchcchcaya araargarcg sgtsaaccay     300
ctsggmaacc tsgtsatyac ytggggmgcy caracyttca arcaycargc yttcaacaar     360
ctsgcsaacc tsttcatyct saacaacaar aaracyatyc chaacaacct sgtsgaraac     420
tacctsacyc cyatgtcmct sgcytactgg ttcatggayg ayggmggmaa rtgggaytac     480
aacaaraact cmacyaacaa rtcmatygts ctsaacacyc artcmttcac yttcgargar     540
gtsgartacc tsgtsaargg mctscgsaac aarttccarc tsaactgyta cgtsaagaty     600
aacaaraaca arccyatyat ctacatygay tcmatgtcmt acctsatytt ctacaacctg     660
```

```
atyaarccht acctsatycc hcaratgatg tacaarctsc chaacacyat ytcmtcmgar    720
acyttcctsa ar                                                       732
```

<210> SEQ ID NO 4
<211> LENGTH: 732
<212> TYPE: DNA
<213> ORGANISM: Artificial
<220> FEATURE:
<223> OTHER INFORMATION: preferred synthetic DNA sequence encoding
      I-SceI (UIPAC code)

<400> SEQUENCE: 4

```
atggccaagc ctcccaagaa gaagcgcaaa gtgaacatca agaagaacca ggtgatgaac     60
ctgggaccta acagcaagct cctgaaggag tacaagagcc agctgatcga actgaacatc    120
gagcagttcg aagctggcat cggcctgatc ctgggcgatg cctacatcag atcccgggac    180
gaaggcaaga cctactgcat gcagttcgag tggaagaaca aggcctacat ggaccacgtg    240
tgtctgctgt acgaccagtg ggtcctgagc cctcctcaca agaaggagcg cgtgaaccat    300
ctgggcaacc tcgtgatcac ctggggagcc cagaccttca gcaccaggc cttcaacaag    360 ctggccaacc tgttcatcgt gaacaacaag aagaccatcc ccaacaacct cgtggagaac    420
tacctcactc ccatgagcct ggcctactgg ttcatggacg acggaggcaa gtgggactac    480
aacaagaaca gcaccaacaa gtcaattgtg ctgaacaccc aaagcttcac cttcgaagaa    540
gtggagtacc tcgtcaaggg cctgcgcaac aagttccagc tgaactgcta cgtgaagatc    600
aacaagaaca agcctatcat ctacatcgac agcatgagct acctgatctt ctacaacctg    660
atcaagccat acctgatccc tcagatgatg tacaagctgc ccaacaccat cagcagcgag    720
accttcctga ag                                                       732
```

<210> SEQ ID NO 5
<211> LENGTH: 3262
<212> TYPE: DNA
<213> ORGANISM: Artificial
<220> FEATURE:
<223> OTHER INFORMATION: T-DNA of pTTAM78 (target locus)
<220> FEATURE:
<221> NAME/KEY: misc_feature
<222> LOCATION: (1)..(25)
<223> OTHER INFORMATION: Right T-DNA border sequence
<220> FEATURE:
<221> NAME/KEY: misc_feature
<222> LOCATION: (26)..(72)
<223> OTHER INFORMATION: synthetic polylinker sequence
<220> FEATURE:
<221> NAME/KEY: misc_feature
<222> LOCATION: (73)..(333)
<223> OTHER INFORMATION: 3' nos (complement)
<220> FEATURE:
<221> NAME/KEY: misc_feature
<222> LOCATION: (334)..(351)
<223> OTHER INFORMATION: synthetic polylinker sequence
<220> FEATURE:
<221> NAME/KEY: misc_feature
<222> LOCATION: (352)..(903)
<223> OTHER INFORMATION: bar sequence (complement)
<220> FEATURE:
<221> NAME/KEY: misc_feature
<222> LOCATION: (904)..(928)
<223> OTHER INFORMATION: synthetic polylinker sequence
<220> FEATURE:
<221> NAME/KEY: misc_feature
<222> LOCATION: (929)..(946)
<223> OTHER INFORMATION: I-SceI recognition site
<220> FEATURE:
<221> NAME/KEY: misc_feature
<222> LOCATION: (947)..(967)

```
<223> OTHER INFORMATION: synthetic polylinker sequence
<220> FEATURE:
<221> NAME/KEY: misc_feature
<222> LOCATION: (968)..(1171)
<223> OTHER INFORMATION: 3'g7
<220> FEATURE:
<221> NAME/KEY: misc_feature
<222> LOCATION: (1172)..(1290)
<223> OTHER INFORMATION: synthetic polylinker sequence
<220> FEATURE:
<221> NAME/KEY: misc_feature
<222> LOCATION: (1291)..(1577)
<223> OTHER INFORMATION: promoter nopaline synthetase gene
<220> FEATURE:
<221> NAME/KEY: misc_feature
<222> LOCATION: (1578)..(1590)
<223> OTHER INFORMATION: synthetic polylinker sequence
<220> FEATURE:
<221> NAME/KEY: misc_feature
<222> LOCATION: (1591)..(2394)
<223> OTHER INFORMATION: nptII
<220> FEATURE:
<221> NAME/KEY: misc_feature
<222> LOCATION: (2395)..(2567)
<223> OTHER INFORMATION: 3' neo
<220> FEATURE:
<221> NAME/KEY: misc_feature
<222> LOCATION: (2568)..(3183)
<223> OTHER INFORMATION: 3' ocs
<220> FEATURE:
<221> NAME/KEY: misc_feature
<222> LOCATION: (3184)..(3234)
<223> OTHER INFORMATION: synthetic polylinker sequence
<220> FEATURE:
<221> NAME/KEY: misc_feature
<222> LOCATION: (3235)..(3262)
<223> OTHER INFORMATION: left T-DNA border sequence

<400> SEQUENCE: 5
aattacaacg gtatatatcc tgccagtact cggccgtcga cctgcaggca attggtacct    60
agaggatctt cccgatctag taacatagat gacaccgcgc gcgataattt atcctagttt   120
gcgcgctata ttttgttttc tatcgcgtat taaatgtata attgcgggac tctaatcata   180
aaaacccatc tcataaataa cgtcatgcat tacatgttaa ttattacatg cttaacgtaa   240
ttcaacagaa attatatgat aatcatcgca agaccggcaa caggattcaa tcttaagaaa   300
ctttattgcc aaatgtttga acgatctgct tcggatccta gacgcgtgag atcagatctc   360
ggtgacgggc aggaccggac ggggcggtac cggcaggctg aagtccagct gccagaaacc   420
cacgtcatgc cagttcccgt gcttgaagcc ggccgcccgc agcatgccgc gggggggcata   480 tccgagcgcc tcgtgcatgc gcacgctcgg gtcgttgggc agcccgatga cagcgaccac   540
gctcttgaag ccctgtgcct ccagggactt cagcaggtgg gtgtagagcg tggagcccag   600
tcccgtccgc tggtggcggg gggagacgta cacggtcgac tcggccgtcc agtcgtaggc   660
gttgcgtgcc ttccaggggc ccgcgtaggc gatgccggcg acctcgccgt ccacctcggc   720
gacgagccag ggatagcgct cccgcagacg gacgaggtcg tccgtccact cctgcggttc   780
ctgcggctcg gtacggaagt tgaccgtgct tgtctcgatg tagtggttga cgatggtgca   840
gaccgccggc atgtccgcct cggtggcacg gcggatgtcg gccgggcgtc gttctgggtc   900
catggttata gagagagaga tagatttaat taccctgtta tccctaggcc gctgtacagg   960
gcccgggatc ttgaaagaaa tatagtttaa atatttattg ataaaataac aagtcaggta  1020
ttatagtcca agcaaaaaca taaatttatt gatgcaagtt taaattcaga aatatttcaa  1080
taactgatta tatcgctgg  tacattgccg tagatgaaag actgagtgcg atattatgtg  1140
taatacataa attgatgata tagctagctt aggcgcgcca tagatcccgt caattctcac  1200
```

```
tcattaggca ccccaggctt tacactttat gcttccggct cgtataatgt gtggaattgt    1260
gagcggataa caatttcaca caggaaacag gatcatgagc ggagaattaa gggagtcacg    1320
ttatgacccc cgccgatgac gcgggacaag ccgttttacg tttggaactg acagaaccgc    1380
aacgattgaa ggagccactc agccgcgggt ttctggagtt taatgagcta agcacatacg    1440
tcagaaacca ttattgcgcg ttcaaaagtc gcctaaggtc actatcagct agcaaatatt    1500
tcttgtcaaa aatgctccac tgacgttcca taaattcccc tcggtatcca attagagtct    1560
catattcact ctcaatcaaa gatccggccc atgatcatgt ggattgaaca agatggattg    1620
cacgcaggtt ctccggccgc ttgggtggag aggctattcg gctatgactg ggcacaacag    1680
acaatcggct gctctgatgc cgccgtgttc cggctgtcag cgcaggggcg cccggttctt    1740
tttgtcaaga ccgacctgtc cggtgccctg aatgaactgc aggacgaggc agcgcggcta    1800
tcgtggctgg ccacgacggg cgttccttgc gcagctgtgc tcgacgttgt cactgaagcg    1860
ggaagggact ggctgctatt gggcgaagtg ccggggcagg atctcctgtc atctcacctt    1920
gctcctgccg agaaagtatc catcatggct gatgcaatgc ggcggctgca tacgcttgat    1980
ccggctacct gcccattcga ccaccaagcg aaacatcgca tcgagcgagc acgtactcgg    2040
atggaagccg gtcttgtcga tcaggatgat ctggacgaag agcatcaggg gctcgcgcca    2100
gccgaactgt tcgccaggct caaggcgcgc atgcccgacg gcgaggatct cgtcgtgacc    2160
catggcgatg cctgcttgcc gaatatcatg gtggaaaatg gccgcttttc tggattcatc    2220
gactgtggcc ggctgggtgt ggcggaccgc tatcaggaca tagcgttggc tacccgtgat    2280
attgctgaag agcttggcgg cgaatgggct gaccgcttcc tcgtgcttta cggtatcgcc    2340
gctcccgatt cgcagcgcat cgccttctat cgccttcttg acgagttctt ctgagcggga    2400
ctctggggtt cgaaatgacc gaccaagcga cgcccaacct gccatcacga gatttcgatt    2460
ccaccgccgc cttctatgaa aggttgggct tcggaatcgt tttccgggac gccggctgga    2520
tgatcctcca gcgcggggat ctcatgctgg agttcttcgc ccacccctg ctttaatgag    2580
atatgcgaga cgcctatgat cgcatgatat ttgctttcaa ttctgttgtg cacgttgtaa    2640
aaaacctgag catgtgtagc tcagatcctt accgccggtt tcggttcatt ctaatgaata    2700
tatcacccgt tactatcgta ttttatgaa taatattctc cgttcaattt actgattgta    2760
ccctactact tatatgtaca atattaaaat gaaaacaata tattgtgctg aataggttta    2820
tagcgacatc tatgatagag cgccacaata acaaacaatt gcgttttatt attacaaatc    2880
caattttaaa aaaagcggca gaaccggtca aacctaaaag actgattaca taaatcttat    2940
tcaaatttca aaaggcccca ggggctagta tctacgacac accgagcggc gaactaataa    3000
cgttcactga agggaactcc ggttccccgc cggcgcgcat gggtgagatt ccttgaagtt    3060
gagtattggc cgtccgctct accgaaagtt acgggcacca ttcaacccgg tccagcacgg    3120
cggccgggta accgacttgc tgccccgaga attatgcagc attttttttgg tgtatgtggg    3180
ccctgtacag cggccgcgtt aacgcgtata ctctagagcg atcgccatgg agccatttac    3240
aattgaatat atcctgccgc cg                                             3262
```

<210> SEQ ID NO 6  
<211> LENGTH: 5345  
<212> TYPE: DNA  
<213> ORGANISM: Artificial  
<220> FEATURE:  
<223> OTHER INFORMATION: T-DNA of pTTA82 (repair DNA)  
<220> FEATURE:  
<221> NAME/KEY: misc_feature  
<222> LOCATION: (1)..(25)

-continued

```
<223> OTHER INFORMATION: right T-DNA border sequence
<220> FEATURE:
<221> NAME/KEY: misc_feature
<222> LOCATION: (26)..(62)
<223> OTHER INFORMATION: synthetic polylinker sequence
<220> FEATURE:
<221> NAME/KEY: misc_feature
<222> LOCATION: (63)..(578)
<223> OTHER INFORMATION: bar 3' deleted (complement)
<220> FEATURE:
<221> NAME/KEY: misc_feature
<222> LOCATION: (579)..(603)
<223> OTHER INFORMATION: synthetic polylinker sequence
<220> FEATURE:
<221> NAME/KEY: misc_feature
<222> LOCATION: (604)..(616)
<223> OTHER INFORMATION: partial I-SceI site
<220> FEATURE:
<221> NAME/KEY: misc_feature
<222> LOCATION: (617)..(1429)
<223> OTHER INFORMATION: P35S3 (complement)
<220> FEATURE:
<221> NAME/KEY: misc_feature
<222> LOCATION: (1430)..(1438)
<223> OTHER INFORMATION: partial I-SceI site
<220> FEATURE:
<221> NAME/KEY: misc_feature
<222> LOCATION: (1460)..(1663)
<223> OTHER INFORMATION: 3' gene 7
<220> FEATURE:
<221> NAME/KEY: misc_feature
<222> LOCATION: (1664)..(1782)
<223> OTHER INFORMATION: synthetic polylinker sequence
<220> FEATURE:
<221> NAME/KEY: misc_feature
<222> LOCATION: (1783)..(2069)
<223> OTHER INFORMATION: promoter of the nopaline synthetase gene
<220> FEATURE:
<221> NAME/KEY: misc_feature
<222> LOCATION: (2070)..(2082)
<223> OTHER INFORMATION: synthetic polylinker sequence
<220> FEATURE:
<221> NAME/KEY: misc_feature
<222> LOCATION: (2083)..(2886)
<223> OTHER INFORMATION: nptII
<220> FEATURE:
<221> NAME/KEY: misc_feature
<222> LOCATION: (2887)..(3059)
<223> OTHER INFORMATION: 3' neo
<220> FEATURE:
<221> NAME/KEY: misc_feature
<222> LOCATION: (3060)..(3675)
<223> OTHER INFORMATION: 3' ocs
<220> FEATURE:
<221> NAME/KEY: misc_feature
<222> LOCATION: (3676)..(3731)
<223> OTHER INFORMATION: synthetic polylinker sequence
<220> FEATURE:
<221> NAME/KEY: misc_feature
<222> LOCATION: (3732)..(4246)
<223> OTHER INFORMATION: P35S2
<220> FEATURE:
<221> NAME/KEY: misc_feature
<222> LOCATION: (4247)..(4289)
<223> OTHER INFORMATION: Ats1BL
<220> FEATURE:
<221> NAME/KEY: misc_feature
<222> LOCATION: (4290)..(4322)
<223> OTHER INFORMATION: NLS
<220> FEATURE:
<221> NAME/KEY: misc_feature
<222> LOCATION: (4323)..(5023)
<223> OTHER INFORMATION: I-SceI defective
<220> FEATURE:
<221> NAME/KEY: misc_feature
<222> LOCATION: (5024)..(5260)
<223> OTHER INFORMATION: 3' 35S
<220> FEATURE:
<221> NAME/KEY: misc_feature
<222> LOCATION: (5261)..(5317)
```

```
<223> OTHER INFORMATION: synthetic polylinker sequence
<220> FEATURE:
<221> NAME/KEY: misc_feature
<222> LOCATION: (5318)..(5345)
<223> OTHER INFORMATION: left T-DNA border sequence

<400> SEQUENCE: 6
aattacaacg gtatatatcc tgccagtact cggccgtcga cctgcaggca attggtacga      60
tcctagacgc gtgagatcag atcctgccag aaacccacgt catgccagtt cccgtgcttg     120
aagccggccg cccgcagcat gccgcggggg gcatatccga gcgcctcgtg catgcgcacg     180
ctcgggtcgt tgggcagccc gatgacacgc accacgctct tgaagccctg tgcctccagg     240
gacttcagca ggtgggtgta gagcgtggag cccagtcccg tccgctggtg gcggggggag     300
acgtacacgg tcgactcggc cgtccagtcg taggcgttgc gtgccttcca ggggcccgcg     360
taggcgatgc cggcgacctc gccgtccacc tcggcgacga gccagggata gcgctcccgc     420
agacggacga ggtcgtccgt ccactcctgc ggttcctgcg gctcggtacg gaagttgacc     480
gtgcttgtct cgatgtagtg gttgacgatg gtgcagaccg ccggcatgtc cgcctcggtg     540
gcacggcgga tgtcggccgg gcgtcgttct gggtccatgg ttatagagag agagatagat     600
ttaattaccc tgttattaga gagagactgg tgatttcagc gtgtcctctc caaatgaaat     660
gaacttcctt atatagagga agggtcttgc gaaggatagt gggattgtgc gtcatccctt     720
acgtcagtgg agatgtcaca tcaatccact tgctttgaag acgtggttgg aacgtcttct     780
ttttccacga tgctcctcgt gggtgggggt ccatctttgg gaccactgtc ggcagaggca     840
tcttgaatga tagcctttcc tttatcgcaa tgatggcatt tgtaggagcc accttccttt     900
tctactgtcc tttcgatgaa gtgacagata gctgggcaat ggaatccgag gaggtttccc     960
gaaattatcc tttgttgaaa agtctcaata gcccttttggt cttctgagac tgtatctttg    1020
acatttttgg agtagaccag agtgtcgtgc tccaccatgt tgacgaagat tttcttcttg    1080
tcattgagtc gtaaaagact ctgtatgaac tgttcgccag tcttcacggc gagttctgtt    1140
agatcctcga tttgaatctt agactccatg catggcctta gattcagtag gaactacctt    1200
tttagagact ccaatctcta ttacttgcct tggtttatga agcaagcctt gaatcgtcca    1260
tactggaata gtacttctga tcttgagaaa tatgtctttc tctgtgttct tgatgcaatt    1320
agtcctgaat cttttgactg catctttaac cttcttggga aggtatttga tctcctggag    1380
attgttactc gggtagatcg tcttgatgag acctgctgcg taggaacgct tatccctagg    1440
ccgctgtaca gggcccggga tcttgaaaga aatatagttt aaatatttat tgataaaata    1500
acaagtcagg tattatagtc caagcaaaaa cataaattta ttgatgcaag tttaaattca    1560
gaaatatttc aataactgat tatatcagct ggtacattgc cgtagatgaa agactgagtg    1620
cgatattatg tgtaatacat aaattgatga tatagctagc ttaggcgcgc catagatccc    1680
gtcaattctc actcattagg caccccaggc tttacacttt atgcttccgg ctcgtataat    1740
gtgtggaatt gtgagcggat aacaatttca cacaggaaac aggatcatga gcggagaatt    1800
aagggagtca cgttatgacc cccgccgatg acgcgggaca agccgtttta cgtttggaac    1860
tgacagaacc gcaacgattg aaggagccac tcagccgcgg gtttctggag tttaatgagc    1920
taagcacata cgtcagaaac cattattgcg cgttcaaaag tcgcctaagg tcactatcag    1980
ctagcaaata tttcttgtca aaaatgctcc actgacgttc cataaattcc cctcggtatc    2040
caattagagt ctcatattca ctctcaatca aagatccggc ccatgatcat gtggattgaa    2100
caagatggat tgcacgcagg ttctccggcc gcttgggtgg agaggctatt cggctatgac    2160
```

```
tgggcacaac agacaatcgg ctgctctgat gccgccgtgt tccggctgtc agcgcagggg    2220
cgcccggttc tttttgtcaa gaccgacctg tccggtgccc tgaatgaact gcaggacgag    2280
gcagcgcggc tatcgtggct ggccacgacg ggcgttcctt gcgcagctgt gctcgacgtt    2340
gtcactgaag cgggaaggga ctggctgcta ttgggcgaag tgccggggca ggatctcctg    2400
tcatctcacc ttgctcctgc cgagaaagta tccatcatgg ctgatgcaat gcggcggctg    2460
catacgcttg atccggctac ctgcccattc gaccaccaag cgaaacatcg catcgagcga    2520
gcacgtactc ggatggaagc cggtcttgtc gatcaggatg atctggacga agagcatcag    2580
gggctcgcgc cagccgaact gttcgccagg ctcaaggcgc gcatgcccga cggcgaggat    2640
ctcgtcgtga cccatggcga tgcctgcttg ccgaatatca tggtggaaaa tggccgcttt    2700
tctggattca tcgactgtgg ccggctgggt gtggcggacc gctatcagga catagcgttg    2760
gctacccgtg atattgctga gagcttggc ggcgaatggg ctgaccgctt cctcgtgctt    2820
tacggtatcg ccgtcccga ttcgcagcgc atcgccttct atcgccttct tgacgagttc    2880
ttctgagcgg gactctgggg ttcgaaatga ccgaccaagc gacgcccaac ctgccatcac    2940
gagatttcga ttccaccgcc gccttctatg aaaggttggg cttcggaatc gttttccggg    3000
acgccggctg gatgatcctc cagcgcgggg atctcatgct ggagttcttc gcccacccc     3060 tgctttaatg agatatgcga gacgcctatg atcgcatgat atttgctttc aattctgttg    3120
tgcacgttgt aaaaaacctg agcatgtgta gctcagatcc ttaccgccgg tttcggttca    3180
ttctaatgaa tatatcaccc gttactatcg tatttttatg aataatattc tccgttcaat    3240
ttactgattg taccctacta cttatatgta caatattaaa atgaaaacaa tatattgtgc    3300
tgaataggtt tatagcgaca tctatgatag agcgccacaa taacaaacaa ttgcgtttta    3360
ttattacaaa tccaatttta aaaaaagcgg cagaaccggt caaacctaaa agactgatta    3420
cataaatctt attcaaattt caaaaggccc caggggctag tatctacgac acaccgagcg    3480
gcgaactaat aacgttcact gaagggaact ccggttcccc gccggcgcgc atgggtgaga    3540
ttccttgaag ttgagtattg gccgtccgct ctaccgaaag ttacgggcac cattcaaccc    3600
ggtccagcac ggcggccggg taaccgactt gctgccccga gaattatgca gcattttttt    3660
ggtgtatgtg ggccctgtac agcggccgcg ttaacgcgta tactctagta tgcaccatac    3720
atggagtcaa aaattcagat cgaggatcta acagaactcg ccgtgaagac tggcgaacag    3780
ttcatacaga gtctttttacg actcaatgac aagaagaaaa tcttcgtcaa catggtggag    3840
cacgacactc tcgtctactc caagaatatc aaagatacag tctcagaaga ccaaagggct    3900
attgagactt ttcaacaaag ggtaatatcg ggaaacctcc tcggattcca ttgcccagct    3960
atctgtcact tcatcaaaag gacagtagaa aaggaaggtg gcacctacaa atgccatcat    4020
tgcgataaag gaaaggctat cgttcaagat gcctctgccg acagtggtcc caaagatgga    4080
cccccaccca cgaggagcat cgtggaaaaa gaagacgttc caaccacgtc ttcaaagcaa    4140
gtggattgat gtgatatctc cactgacgta agggatgacg cacaatccca ctatccttcg    4200
caagaccctt cctctatata aggaagttca tttcatttgg agaggactcg agaattaagc    4260
aaaagaagaa gaagaagaag tccaaaacca tggctaaacc cccaagaag aagcgcaagg    4320 ttaacatcaa aaaaaccag gtaatgaacc tgggtccgaa ctctaaactg ctgaaagaat    4380
acaaatccca gctgatcgaa ctgaacatcg aacagttcga agcaggtatc ggtctgatcc    4440
tgggtgatgc ttcatccgt tctcgtgatg aaggtaaaac ctactgtatg cagttcgagt    4500
ggaaaaacaa agcatacatg gaccacgtat gtctgctgta cgatcagtgg gtactgtccc    4560
```

```
cgccgcacaa aaaagaacgt gttaaccacc tgggtaacct ggtaatcacc tggggcgccc    4620
agactttcaa acaccaagct ttcaacaaac tggctaacct gttcatcgtt aacaacaaaa    4680
aaaccatccc gaacaacctg gttgaaaact acctgacccc gatgtctctg catactggt    4740 tcatggatga tggtggtaaa tgggattaca acaaaaactc taccaacaaa gtattgtact    4800
gaacacccag tctttcactt tcgaagaagt agaatacctg gttaagggtc tgcgtaacaa    4860
attccaactg aactgttacg taaaaatcaa caaaaacaaa ccgatcatct acatcgattc    4920
tatgtcttac ctgatcttct acaacctgat caaaccgtac ctgatcccgc agatgatgta    4980
caaactgccg aacactatct cctccgaaac tttcctgaaa tagggctagc aagcttggac    5040
acgctgaaat caccagtctc tctctacaaa tctatctctc tctattttct ccataataat    5100
gtgtgagtag ttcccagata agggaattag ggttcctata gggtttcgct catgtgttga    5160
gcatataaga aacccttagt atgtatttgt atttgtaaaa tacttctatc aataaaattt    5220
ctaattccta aaaccaaaat ccagtactaa aatccagatc atgcatggta cagcggccgc    5280
gttaacgcgt atactctaga gcgatcgcca tggagccatt tacaattgaa tatatcctgc    5340
cgccg                                                                5345

<210> SEQ ID NO 7
<211> LENGTH: 4066
<212> TYPE: DNA
<213> ORGANISM: Artificial
<220> FEATURE:
<223> OTHER INFORMATION: pCV78
<220> FEATURE:
<221> NAME/KEY: misc_feature
<222> LOCATION: (234)..(763)
<223> OTHER INFORMATION: P35S2 promoter
<220> FEATURE:
<221> NAME/KEY: misc_feature
<222> LOCATION: (764)..(805)
<223> OTHER INFORMATION: Ats1b'
<220> FEATURE:
<221> NAME/KEY: misc_feature
<222> LOCATION: (808)..(839)
<223> OTHER INFORMATION: nuclear localization signal
<220> FEATURE:
<221> NAME/KEY: misc_feature
<222> LOCATION: (840)..(1541)
<223> OTHER INFORMATION: I-SceI synthetic
<220> FEATURE:
<221> NAME/KEY: misc_feature
<222> LOCATION: (1544)..(1792)
<223> OTHER INFORMATION: 3' 35S
<220> FEATURE:
<221> NAME/KEY: misc_feature
<222> LOCATION: (3006)..(3886)
<223> OTHER INFORMATION: Ampicillin resistance (complement)

<400> SEQUENCE: 7
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctggc ttaactatg cggcatcaga gcagattgta ctgagagtgc    180
accatacctg caggcaattg gtacctacgt atgcatggcg cgccatatgc accatacatg    240
gagtcaaaaa ttcagatcga ggatctaaca gaactcgccg tgaagactgg cgaacagttc    300
atacagagtc ttttacgact caatgacaag aagaaaatct tcgtcaacat ggtggagcac    360
gacactctcg tctactccaa gaatatcaaa gatacagtct cagaagacca aagggctatt    420 gagactttc aacaagggt aatatcggga aacctcctcg gattccattg cccagctatc    480
tgtcacttca tcaaaaggac agtagaaaag gaaggtggca cctacaaatg ccatcattgc    540
```

-continued

```
gataaaggaa aggctatcgt tcaagatgcc tctgccgaca gtggtcccaa agatggaccc   600
ccacccacga ggagcatcgt ggaaaaagaa gacgttccaa ccacgtcttc aaagcaagtg   660
gattgatgtg atatctccac tgacgtaagg gatgacgcac aatcccacta tccttcgcaa   720
gacccttcct ctatataagg aagttcattt catttggaga ggactcgaga attaagcaaa   780
agaagaagaa gaagaagtcc aaaaccatgg ccaagcctcc caagaagaag cgcaaagtga   840
acatcaagaa gaaccaggtg atgaacctgg gacctaacag caagctcctg aaggagtaca   900
agagccagct gatcgaactg aacatcgagc agttcgaagc tggcatcggc ctgatcctgg   960
gcgatgccta catcagatcc cgggacgaag gcaagaccta ctgcatgcag ttcgagtgga  1020
agaacaaggc ctacatggac cacgtgtgtc tgctgtacga ccagtgggtc ctgagccctc  1080
ctcacaagaa ggagcgcgtg aaccatctgg gcaacctcgt gatcacctgg ggagcccaga  1140
ccttcaagca ccaggccttc aacaagctgg ccaacctgtt catcgtgaac aacaagaaga  1200
ccatccccaa caacctcgtg gagaactacc tcactcccat gagcctggcc tactggttca  1260
tggacgacgg aggcaagtgg gactacaaca agaacagcac caacaagtca attgtgctga  1320
acacccaaag cttcaccttc gaagaagtgg agtacctcgt caagggcctg cgcaacaagt  1380
tccagctgaa ctgctacgtg aagatcaaca agaacaagcc tatcatctac atcgacagca  1440
tgagctacct gatcttctac aacctgatca agccataccT gatccctcag atgatgtaca  1500
agctgcccaa caccatcagc agcgagacct tcctgaagtg aggctagcaa gcttggacac  1560
gctgaaatca ccagtctctc tctacaaatc tatctctctc tattttctcc ataataatgt  1620
gtgagtagtt cccagataag ggaattaggg ttcctatagg gtttcgctca tgtgttgagc  1680
atataagaaa cccttagtat gtatttgtat ttgtaaaata cttctatcaa taaaatttct  1740
aattcctaaa accaaaatcc agtactaaaa tccagatcat gcatggtaca gcggccgcgt  1800
taacgcgtat actctagagc gatcgcaagc ttggcgtaat catggtcata gctgtttcct  1860
gtgtgaaatt gttatccgct cacaattcca cacaacatac gagccggaag cataaagtgt  1920
aaagcctggg gtgcctaatg agtgagctaa ctcacattaa ttgcgttgcg ctcactgccc  1980
gctttccagt cgggaaacct gtcgtgccag ctgcattaat gaatcggcca acgcgcgggg  2040
agaggcggtt tgcgtattgg gcgctcttcc gcttcctcgc tcactgactc gctgcgctcg  2100
gtcgttcggc tgcggcgagc ggtatcagct cactcaaagg cggtaatacg gttatccaca  2160
gaatcagggg ataacgcagg aaagaacatg tgagcaaaag gccagcaaaa ggccaggaac  2220
cgtaaaaagg ccgcgttgct ggcgtttttc cataggctcc gcccccctga cgagcatcac  2280
aaaaatcgac gctcaagtca gaggtggcga aacccgacag gactataaag ataccaggcg  2340
tttccccctg gaagctccct cgtgcgctct cctgttccga ccctgccgct taccggatac  2400
ctgtccgcct ttctcccttc gggaagcgtg gcgctttctc aaagctcacg ctgtaggtat  2460
ctcagttcgg tgtaggtcgt tcgctccaag ctgggctgtg tgcacgaacc ccccgttcag  2520
cccgaccgct gcgccttatc cggtaactat cgtcttgagt ccaacccggt aagacacgac  2580
ttatcgccac tggcagcagc cactggtaac aggattagca gagcgaggta tgtaggcggt  2640
gctacagagt tcttgaagtg gtggcctaac tacggctaca ctagaagaac agtatttggt  2700
atctgcgctc tgctgaagcc agttaccttc ggaaaaagag ttggtagctc ttgatccggc  2760
aaacaaacca ccgctggtag cggtggtttt tttgtttgca agcagcagat tacgcgcaga  2820
aaaaaaggat ctcaagaaga tcctttgatc ttttctacgg ggtctgacgc tcagtggaac  2880
gaaaactcac gttaagggat tttggtcatg agattatcaa aaaggatctt cacctagatc  2940
```

```
cttttaaatt aaaaatgaag ttttaaatca atctaaagta tatatgagta aacttggtct   3000
gacagttacc aatgcttaat cagtgaggca cctatctcag cgatctgtct atttcgttca   3060
tccatagttg cctgactccc cgtcgtgtag ataactacga tacgggaggg cttaccatct   3120
ggccccagtg ctgcaatgat accgcgagac ccacgctcac cggctccaga tttatcagca   3180
ataaaccagc cagccggaag ggccgagcgc agaagtggtc ctgcaacttt atccgcctcc   3240
atccagtcta ttaattgttg ccgggaagct agagtaagta gttcgccagt taatagtttg   3300
cgcaacgttg ttgccattgc tacaggcatc gtggtgtcac gctcgtcgtt tggtatggct   3360
tcattcagct ccggttccca acgatcaagg cgagttacat gatccccat gttgtgcaaa    3420 aaagcggtta gctccttcgg tcctccgatc gttgtcagaa gtaagttggc cgcagtgtta   3480
tcactcatgg ttatggcagc actgcataat tctcttactg tcatgccatc cgtaagatgc   3540
ttttctgtga ctggtgagta ctcaaccaag tcattctgag aatagtgtat gcggcgaccg   3600
agttgctctt gcccggcgtc aatacgggat aataccgcgc cacatagcag aactttaaaa   3660
gtgctcatca ttggaaaacg ttcttcgggg cgaaaactct caaggatctt accgctgttg   3720
agatccagtt cgatgtaacc cactcgtgca cccaactgat cttcagcatc ttttactttc   3780
accagcgttt ctgggtgagc aaaaacagga aggcaaaatg ccgcaaaaaa gggaataagg   3840
gcgacacgga aatgttgaat actcatactc ttccttttc aatattattg aagcatttat    3900
cagggttatt gtctcatgag cggatacata tttgaatgta tttagaaaaa taaacaaata   3960
ggggttccgc gcacatttcc ccgaaaagtg ccacctgacg tctaagaaac cattattatc   4020
atgacattaa cctataaaaa taggcgtatc acgaggccct ttcgtc                  4066
```